(12) United States Patent
Shturman et al.

(10) Patent No.: US 7,174,240 B2
(45) Date of Patent: Feb. 6, 2007

(54) CONTROL SYSTEM FOR ROTATIONAL ANGIOPLASTY DEVICE

(75) Inventors: Leonid Shturman, Greenwich, CT (US); Georgy Vasilevich Morov, Moscow (RU); Vladimir Alekseevich Malgichev, Moscow (RU)

(73) Assignee: Cardiovascular Systems, Inc., St. Paul, MN (US)

( * ) Notice: Subject to any disclaimer, the term of this patent is extended or adjusted under 35 U.S.C. 154(b) by 624 days.

(21) Appl. No.: 10/272,126

(22) Filed: Oct. 16, 2002

(65) Prior Publication Data

US 2003/0120296 A1 Jun. 26, 2003

Related U.S. Application Data

(60) Provisional application No. 60/348,188, filed on Oct. 19, 2001.

(51) Int. Cl.
*G05D 7/00* (2006.01)
*A61B 17/22* (2006.01)

(52) U.S. Cl. .................. 700/282; 700/281; 606/159

(58) Field of Classification Search ............... 700/282, 700/283, 281; 606/159, 150, 167, 169, 170, 606/171, 180; 604/507, 508, 19, 22; 600/466; 607/122
See application file for complete search history.

(56) References Cited

U.S. PATENT DOCUMENTS

| | | | |
|---|---|---|---|
| 4,990,134 A | 2/1991 | Auth | 604/22 |
| 5,314,407 A | 5/1994 | Auth et al. | 604/22 |
| 5,836,868 A | 11/1998 | Ressemann et al. | 606/159 |
| 5,897,566 A | 4/1999 | Shturman et al. | 606/159 |
| 6,024,749 A | 2/2000 | Shturman et al. | 606/159 |
| 6,077,282 A | 6/2000 | Shturman et al. | 606/159 |
| 6,080,170 A * | 6/2000 | Nash et al. | 606/159 |
| 6,113,615 A | 9/2000 | Wulfman | 606/159 |
| 6,129,734 A | 10/2000 | Shturman et al. | 606/159 |
| 6,132,444 A | 10/2000 | Shturman et al. | 606/159 |

* cited by examiner

*Primary Examiner*—Leo Picard
*Assistant Examiner*—Charles Kasenge
(74) *Attorney, Agent, or Firm*—Altera Law Group, LLC

(57) ABSTRACT

A method for controlling fluid flow in a rotational atherectomy device. A source of fluid is provided through a pump to the rotational atherectomy device, wherein the pump maintains the fluid flow at a minimal rate during a time period when a drive shaft of the device is not rotating. A first control is activated to increase a rate of the fluid flow and second control is activated to initiate a rotation of the drive shaft during another time period when the fluid flow is at the increased rate.

17 Claims, 27 Drawing Sheets

CONTROL SYSTEM FOR ROTATIONAL ANGIOPLASTY DEVICE

CROSS-REFERENCE TO RELATED APPLICATION

This application claims benefit of the earlier filed U.S. Provisional Patent Application No. 60/348,188, filing date Oct. 19, 2001.

BACKGROUND OF THE INVENTION

1. Field of the Invention

The present invention generally relates to devices and methods for removing tissue from body passageways and, more particularly, to a control system for a rotational and or orbital angioplasty device.

2. Brief Description of Related Developments

There are a number of different techniques and devices which have been developed for use in removal and/or repair of arteries and other similar body passages. One objective of some of the aforementioned devices and techniques is removal of atherosclerotic plaques from patient's arteries. Atherosclerosis is characterized by buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses. If left untreated, such stenoses can cause angina, hypertension, myocardial infarction, strokes and the like.

Rotational angioplasty procedures are a common technique for removing such stenotic material. Such procedures are used most frequently to commence the opening of calcified lesions in coronary arteries. Often the rotational angioplasty procedure is not used alone, but is followed by a balloon angioplasty procedure. This, in turn, may frequently be followed by placement of a stent to assist in keeping the artery open. For noncalcified lesions, balloon angioplasty most often is used alone to open the artery, with stents often placed to maintain the opened artery. Studies have shown, however, that a significant percentage of patients who have undergone balloon angioplasty and had a stent placed in an artery experience in-stent restenosis (i.e., blockage of the stent) which most frequently develops over a period of time as a result of excessive growth of scar tissue within the stent. Rotational angioplasty devices were utilized in removing the excessive scar tissue from the stents and, thereby were useful in providing assistance in restoring the patency of the arteries.

It should be understood that rotational angioplasty devices and rotational angioplasty procedures are often referred to as rotational atherectomy devices and rotational atherectomy procedures. These terms may be used interchangeably herein.

One example of a rotational angioplasty device is shown in U.S. Pat. No. 4,990,134 (issued to Auth), wherein a front or distal portion of a burr is covered with an abrasive cutting material such as diamond particles. The diamond coated burr is mounted at the distal end of a flexible drive shaft. The burr is rotated at high speeds (typically, e.g., in the range of about 140,000–180,000 rpm) while it is advanced across the stenosis. The burr has a solid cross-section and thus, as the burr is removing stenotic tissue, it blocks blood flow through the artery. Once the burr has been advanced across the stenosis, the artery will have been opened to a diameter equal to or only slightly larger than the maximum outer diameter of the burr. A series of different size burrs may be utilized to open the artery to a desired diameter. U.S. Pat. No. 5,897,566 (issued to Shturman) shows another rotational angioplasty device having a drive shaft made from helically wound wires. A section of the drive shaft has an enlarged diameter. In one embodiment at least a front or distal segment of this enlarged diameter section is covered with an abrasive material to define an abrasive segment of the drive shaft. The enlarged diameter section is hollow. This Shturman Device of the '566 patent is capable of opening an artery only to a diameter about equal to the maximum diameter of the enlarged diameter section of the drive shaft, thereby providing results similar to the Auth Device of the '134 patent. The Shturman Device of the '566 patent possesses certain advantages over the Auth Device of the '134 patent because it is more flexible. Another example of a rotational angioplasty device is provided in U.S. Pat. No. 6,132,444 (issued to Shturman et al.) describes a rotational atherectomy device having a flexible, elongated, rotatable drive shaft with an eccentric enlarged diameter section. At least part of the eccentric enlarged diameter section has a tissue removing surface with an abrasive surface to define a tissue removing segment of the drive shaft. When placed within an artery against stenotic tissue and rotated at sufficiently high speeds (e.g. in the range of about 40,000 rpm to about 200,000 rpm) the eccentric nature of the enlarged diameter section of the drive shaft causes such section to rotate in such a fashion as to open the stenotic lesion to a diameter substantially larger than the maximum diameter of the enlarged diameter section. Preferably the eccentric enlarged diameter section of the drive shaft has a center of mass spaced radially from the rotational axis of the drive shaft, facilitating the ability of the device to open the stenotic lesion to a diameter substantially larger than the maximum diameter of the enlarged diameter section. A drive shaft having an eccentric enlarged diameter tissue removal section with a diameter of not more than 2 mm is capable of opening stenotic lesions to a diameter equal to the original diameter of the coronary arteries (i.e., to a diameter of more than 3 mm) so that in a significant percentage of cases balloon angioplasty may not be needed to complete the procedure. The device is particularly useful for cleaning out partially blocked stents.

U.S. Pat. No. 5,314,407 to Auth, which is incorporated herein by reference in its entirety, shows the details of a type of an advancer (handle) that may be used in conjunction with rotational atherectomy devices of the type described in Auth '134 patent and Shturman '566 and '444 patents. A handle of the type shown in Auth '407 patent has been commercialized by Heart Technology, Inc. (Redmond, Wash.), now owned by Boston Scientific Corporation (Natick, Mass.), in the rotational atherectomy (angioplasty) device sold under the trademark Rotablator®.

FIG. 1 is an illustration of a rotational angioplasty system 100 of the prior art. As shown in FIG. 1, the prior art system comprises a rotational angioplasty device 104, a fluid supply 106, a gas supply 108, a controller 102 and a foot pedal device 110.

The rotational angioplasty device 104 comprises an advancer assembly 134 that is located within a body or handle 136. A gas driven turbine (not shown) is located within the advancer assembly 134 and rotates a flexible, hollow drive shaft 138. An ablative, diamond coated burr 140 is attached at the distal end of the flexible drive shaft 138. The flexible drive shaft 138 together with the burr 140 may be rotated over a guide wire 141.

As shown in FIG. 1, a flexible sheath 142 extends distally from the handle 136 and surrounds the flexible drive shaft 138 substantially along its entire length.

The advancer assembly 134 also carries a water (saline) pump (not shown). This water pump is located distally to the gas turbine and has a shaft that is connected to the turbine shaft. The output of the fluid pump is in fluid connection with the lumen formed between the flexible drive shaft 138 and the flexible sheath 142.

The rotational angioplasty system 100 shown in FIG. 1 includes an infusion bag 128 to administer a saline solution. The saline bag 128 is pressurized with a pressure cuff 129 to ensure a steady supply of saline to the water pump within the advancer assembly 134 and around the drive shaft 138. The rotation of the gas turbine rotates the fluid pump and increases the fluid flow rate in a lumen between the flexible drive shaft 138 and the sheath 142. The fluid flow rate in this system depends on the rotational speed of the gas turbine. Thus, the fluid acceleration in the lumen between the drive shaft 138 and the sheath 142 can only take place simultaneously with the increase in rotational speed of the gas turbine, and the system can not increase the fluid flow rate in the lumen between the drive shaft 138 and the sheath 142 without increasing the rotational speed of the gas turbine.

A certain amount of static pressure must be applied and maintained against the saline bag 128 in order to provide an adequate fluid flow rate in the lumen between the drive shaft 138 and the sheath 142. This requires repeated repressurization of the pressure cuff 129 disposed around the saline bag 128.

The controller 102 has a front panel 112 that includes a power switch 113, a turbine control knob 114 (adjusts turbine pressure and RPMs), a turbine pressure gauge 115, a turbine (pneumatic) connector 116, a DynaGlide™ (pneumatic) connector 117, and a pair of fiber optic connectors 120. The front panel 112 also includes an event timer 122, a procedure timer 123, and an optical tachometer display 124. The optical tachometer provides or registers information about the rotational speed of the gas turbine of the rotational angioplasty device 104.

The foot pedal 110 is used as an on/off control for the gas turbine of the rotational angioplasty device 104. A DynaGlide™ button 126 is located on the right side of the foot pedal housing 132 and is used as an on/off control for the DynaGlide™ mode of operation.

SUMMARY OF THE INVENTION

The present invention is directed to a method for controlling fluid flow in a rotational atherectomy device. In one embodiment, the method comprises providing a source of fluid through a pump to the rotational atherectomy device, wherein the pump maintains the fluid flow at a minimal rate during a time period during when a drive shaft of the device is not rotating. A method for controlling fluid flow in a rotational atherectomy device. A source of fluid is provided through a pump to the rotational atherectomy device, wherein the pump maintains the fluid flow at a minimal rate during a time period when a drive shaft of the device is not rotating. A first control is activated to increase a rate of the fluid flow and second control is activated to initiate a rotation of the drive shaft during another time period when the fluid flow is at the increased rate.

In one aspect, the present invention is directed to a system for controlling a flow of fluid through a rotational atherectomy device. In one embodiment, the system comprises a controller coupled to the atherectomy device, wherein, the controller comprises a pump control device adapted to control the flow of fluid to the atherectomy device and a drive shaft control device adapted to control a rotation of a drive shaft in the atherectomy device. The system also comprises a fluid supply unit, a first control device coupled to the controller and adapted to increase a flow of fluid to the atherectomy device via the pump control device, and a second control device coupled to the controller and adapted to initiate a rotation of the drive shaft via the drive shaft control device after activation of the first control device.

In another aspect, the present invention is directed to a controller for a rotational atherectomy system. In one embodiment, the system comprises a fluid pump control device adapted to control a pumping of a fluid to a rotational atherectomy device. A turbine control device is adapted to control a rotation of a drive shaft in the rotational atherectomy device. The fluid pump control device comprises a fluid flow controller adapted to provide a pump control signal to a fluid pump, a first control device adapted to provide a pump activation signal to the fluid flow controller and a second control device adapted to provide a turbine activation signal to the fluid flow controller and the turbine control device. Upon activation of the first control device the fluid pump is activated to pump the fluid at a dynamic fluid flow rate and upon activation of the second control device the fluid pump is activated to continue pumping the fluid at the dynamic fluid flow rate while the drive shaft rotates.

In a further aspect, the present invention is directed to a fluid control system for a rotational atherectomy device. In one embodiment a fluid control system comprises a fluid pump connected to the atherectomy device, a fluid supply connected to the fluid pump, a first control switch adapted to initiate a dynamic flow of fluid to the atherectomy device and a second control switch adapted to initiate a second, flow of fluid to the atherectomy device and a rotation of a drive shaft in the atherectomy device.

In yet another aspect, the present invention is directed to a rotational atherectomy system. In one embodiment the system comprises a rotational atherectomy device, a fluid source adapted to supply fluid to the device, a fluid pump system adapted to pump fluid from the fluid source to the device, and a switching mechanism having at least a first mode and a second mode, the first mode adapted to change a state of the fluid pump from a static state to a dynamic state, and the second mode adapted to activate a rotation of a drive shaft in the device.

In one aspect the present invention is directed to a rotational atherectomy system. In one embodiment the system comprises a rotational atherectomy device, a fluid source adapted to supply fluid to the device, a pump system adapted to pump fluid from the fluid source to the device, a first switch adapted to increase a flow of fluid from the fluid source to the device from a first flow rate to a second flow rate when the switch is activated and a second switch adapted to activate a rotation of a drive shaft in the device when the second switch is activated.

In further aspect the present invention is directed to a method for controlling a flow of fluid in a rotational atherectomy device. In one embodiment the method comprises providing a source of fluid through a pump to the rotational atherectomy device, wherein a minimal flow of fluid is maintained through the system when the system is in an idle mode, activating a first control to initiate a first flow of fluid to the device, and activating a second control, wherein activation of the second control includes the steps of initiating a second flow of fluid to the device, and initiating a rotation of a drive shaft of the device, wherein the second flow of fluid to the device is independent of the rotation of the drive shaft.

In a further aspect of the present invention is directed to a method of removing tissue. In one embodiment the method comprises providing a tissue removal device comprising a rotational atherectomy device that includes a fluid pump that is adapted to pump fluid at flow rate independent of a rotational speed of a drive shaft of the atherectomy device, providing a preflush of fluid at an increased rate to a lesion site for predetermined time period prior to the rotation of a drive shaft, activating the rotation of the drive shaft prior to the end of the predetermined time period, wherein the fluid flow rate is maintained at the increased rate during rotation of the drive shaft and the tissue is removed by the rotational atherectomy device and deactivating the rotation of the drive shaft, wherein the fluid flow rate remains at the increased level for another predetermined time period following the deactivation of the rotation of the drive shaft.

In a further aspect the present invention is directed to the method for drawing fluid flow rate around a drive shaft of a rotational angioplasty device. In one embodiment a method comprises providing a fluid pump to pump a fluid around the drive shaft of the device and providing at least two of the controls one of which is used to control the fluid pump and the other to control both the fluid pump and a rotation of the drive shaft of the device, activating a first control to increase fluid flow rate around the drive shaft without initiating rotation of the drive shaft and activating a second control to initiate rotation of the drive shaft and to continue to pump fluid around the drive shaft of the device at an increased fluid flow rate.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 2:
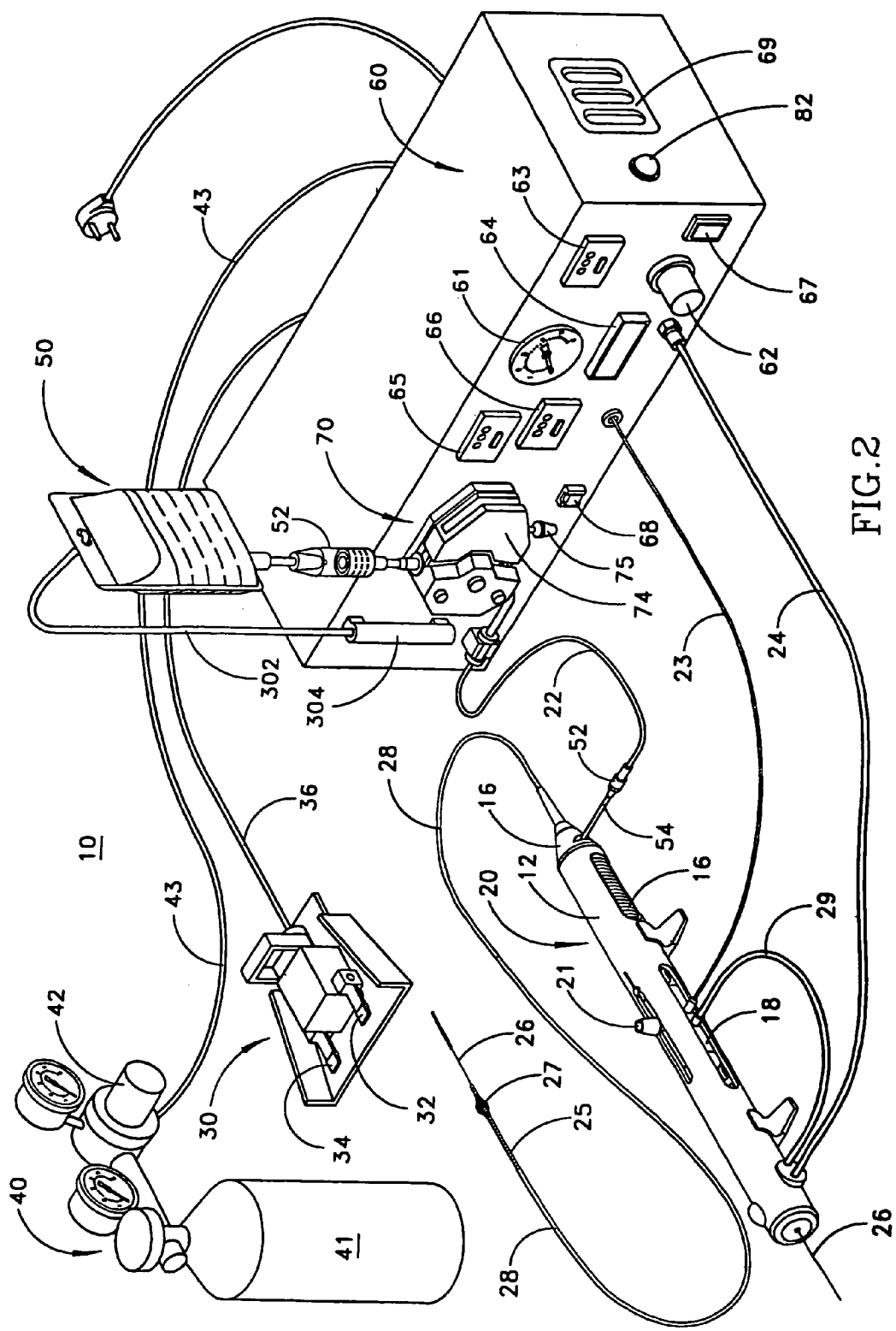
FIG. 2 is a perspective view of one embodiment of a rotational angioplasty system incorporating features of the present invention.

Referring to FIG. 2, there is shown a perspective view of a rotational angioplasty system 10 incorporating features of the present invention. Although the present invention will be described with reference to the embodiment(s) shown in the drawings, it should be understood that the present invention can be embodied in many alternate forms of embodiments. In addition, any suitable size, shape or type of elements or materials could be used.

As shown in FIG. 2, the system 10 generally comprises a rotational angioplasty device ("RAD") 20. The rotational angioplasty device 20 can also comprise, or may be referred to as a rotational atherectomy device. As shown in FIG. 2, the RAD is generally coupled to a controller 60 and a fluid supply 50. The system 10 can also include an activation device 30 and a gas supply system 40. Both the activation device 30 and gas supply system 40 can be coupled or connected to the controller 60. In an alternate embodiment, the system 10 can include such other components suitable for use in a system for removing tissue from a passageway in the body.

Descriptions of some examples of such RAD devices can be found in U.S. Pat. Nos. 5,897,566; 6,024,749; 6,077,282; 6,129,734; and 6,132,444 issued to Shturman, each of which is incorporated herein by reference in its entirety; and in U.S. Pat. Nos. 4,990,134 and 5,314,407 issued to Auth.

As shown in FIG. 2, the RAD 20 can include a prime mover carriage 18 and a drive shaft cartridge 16. A fluid supply line 22, a prime mover speed monitoring line 23, and a gas supply line 24 are adapted to be connected or coupled to the RAD 20. In one embodiment, the lines 22, 23 and 24 can be a physical part of and extend from the RAD 20. In an alternate embodiment, the RAD 20 could include one or more couplings or connection ports to allow one or more of the lines 22, 23 or 24 to be connected to the RAD. Any one of the lines 22, 23 or 24 could be separate from the RAD 20.

Extending from one end of the RAD 20 is an elongated tube 28. The elongated tube 28 can include a rotatable flexible drive shaft 25 that has a tissue removal implement 27 located near the distal end of the flexible drive shaft 25. The elongated tube 28 can also include an inner lumen (not shown) between an interior surface of the elongated tube and the drive shaft 25 along or around which fluid can flow at any suitable or desired rate of flow.

A control knob 21 operatively secured to the prime mover carriage 18 is adapted to facilitate advancing and retracting the prime mover carriage 18 with respect to the housing 12 of the RAD 20.

The prime mover carriage 18 generally carries a prime mover (not shown). Preferably, the prime mover is a compressed gas driven turbine, and for purposes of this description, will be referred to herein as a gas turbine. It should be understood however, that any suitable device can be used to rotate the drive shaft 25 at a desired rotational speed. For example, an electrically powered motor could be used. The gas turbine may be powered, for example, by compressed nitrogen or compressed air supplied from system 40. The system 40 usually includes a tank 41 with compressed gas and a pressure regulator 42.

As shown in FIG. 2, the RAD 20 includes a drive shaft cartridge 16 that includes the elongated tube 28 extending distally from the drive shaft cartridge 16. The rotatable flexible drive shaft 25 is generally disposed within the elongated tube 28. The flexible drive shaft 25 may be rotated over a guide wire 26. A distal portion of the drive shaft 25 may extend distally from the elongated tube 28 and may include the tissue removal implement 27.

Referring to FIG. 2, the RAD 20 can be coupled to the controller 60 through one or more connections, including for example a fluid supply connection, a gas supply connection and a turbine speed monitoring line connection. Fluid is supplied to the drive shaft cartridge 16 from the fluid supply 50 through a fluid supply line 22. As shown in FIG. 2, the fluid supply line 22 is comprised of more than one sequentially connected fluid lines. In alternate embodiments a single line, or any suitable combination of fluid lines may be used. For example, referring to FIG. 2, a short fluid supply line 54 extends from the drive shaft cartridge 16 and is coupled to a longer fluid supply line 22 with a luer lock device 52. The fluid line 54 is connected or coupled to the inner lumen of the elongated tube 28. In an alternate embodiment, the drive shaft cartridge 16 could include a fitting or coupling to which the fluid supply line 22 can be directly connected. In this manner a fluid, such as for example saline, is supplied to the inner lumen of the elongated tube 28 from the fluid supply 50. The fluid supply line 22 could also comprise one or more parallel fluid lines to couple the fluid supply(s) to the inner lumen(s) of the elongated tube 28.

One or more prime mover speed monitoring lines 23 may be used to monitor the rotational speed of the gas turbine. For example, in one embodiment the line 23 could comprise a fiber optic line that is adapted to couple pulses of light from an element of an optical tachometer (not shown) of the RAD 20 to the controller 60. The number of such pulses per unit of time can be used to determine a rotational speed of the gas turbine. In an alternate embodiment any suitable device can be used to communicate the rotational speed of the gas turbine of the RAD 20 to the controller 60.

The gas supply line 24 is used to provide a compressed gas to the guide wire brake (not shown) and further via gas supply line 29 to the prime mover carriage 18 to power the prime mover or gas turbine. As shown in FIG. 2, the gas supply system 40 is a compressed gas system that can provide a steady flow of gas to the controller 60. Generally, any conventional or suitable system 40 can be used to supply the flow of compressed gas via a gas line 43 to the controller 60. As shown in FIG. 2, the compressed gas system 40 comprises one or more tanks or bottles 41 coupled to a regulator device 42. In an alternate embodiment, the gas system could comprise a hospital gas system where the supply of compressed gas is generally delivered via a compressed gas line 43 to the controller unit 60.

As shown in FIG. 2, the system 10 can also include a fluid pump 70. The fluid pump 70 is generally adapted to pump the fluid from the fluid supply 50 through the fluid supply line 22 to an inner lumen(s) of the elongated tube 28 and to some other moving parts of the RAD. Although the elongated tube 28 is referred to herein as generally having a lumen, in alternate embodiments, the elongated tube 28 could also include a plurality of lumens.

Figure 3:
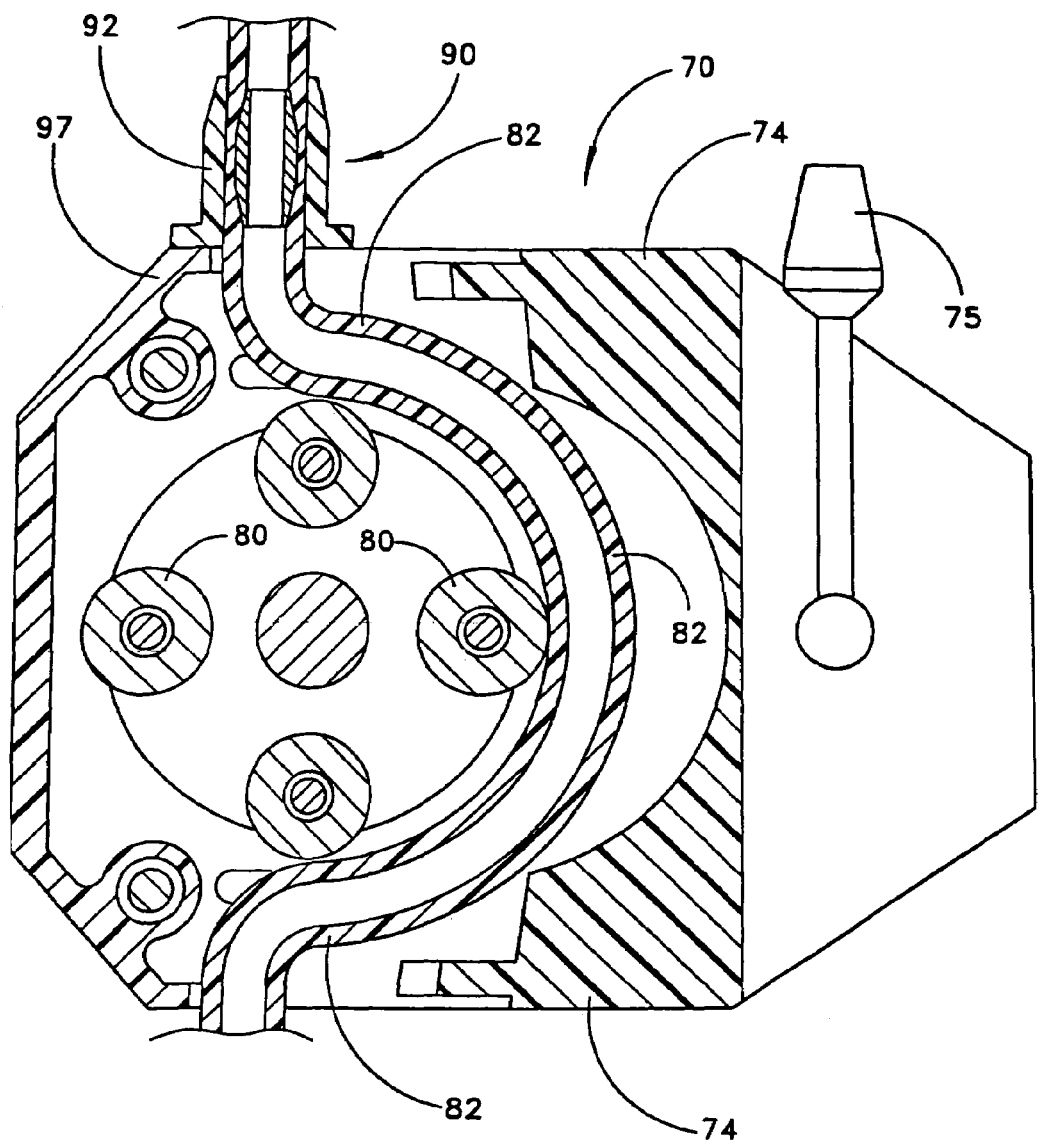
FIG. 3 is a cross-sectional view of one embodiment of a roller pump.
Figure 4:
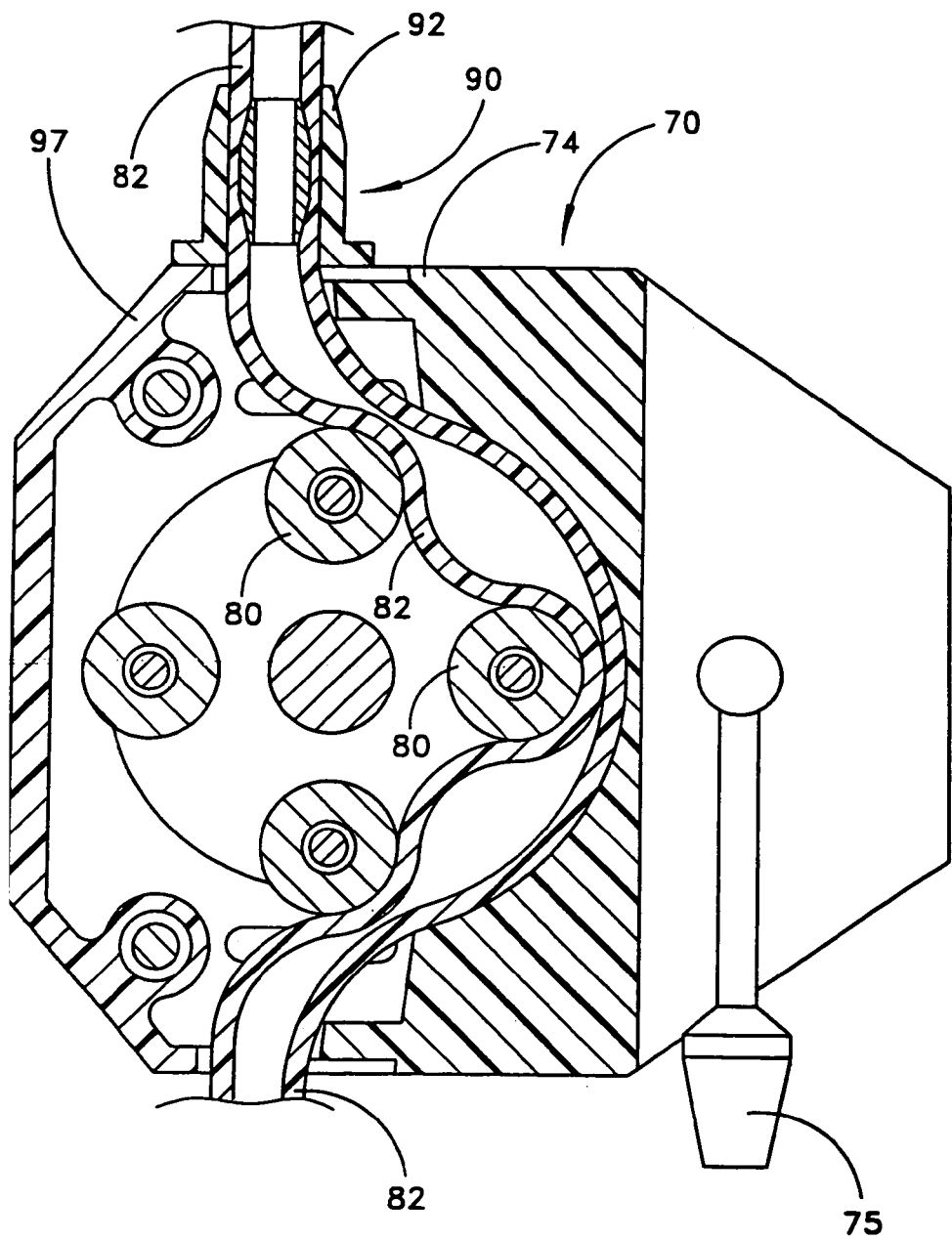
FIG. 4 is a cross-sectional view of a roller pump in a closed position.
Figure 5:
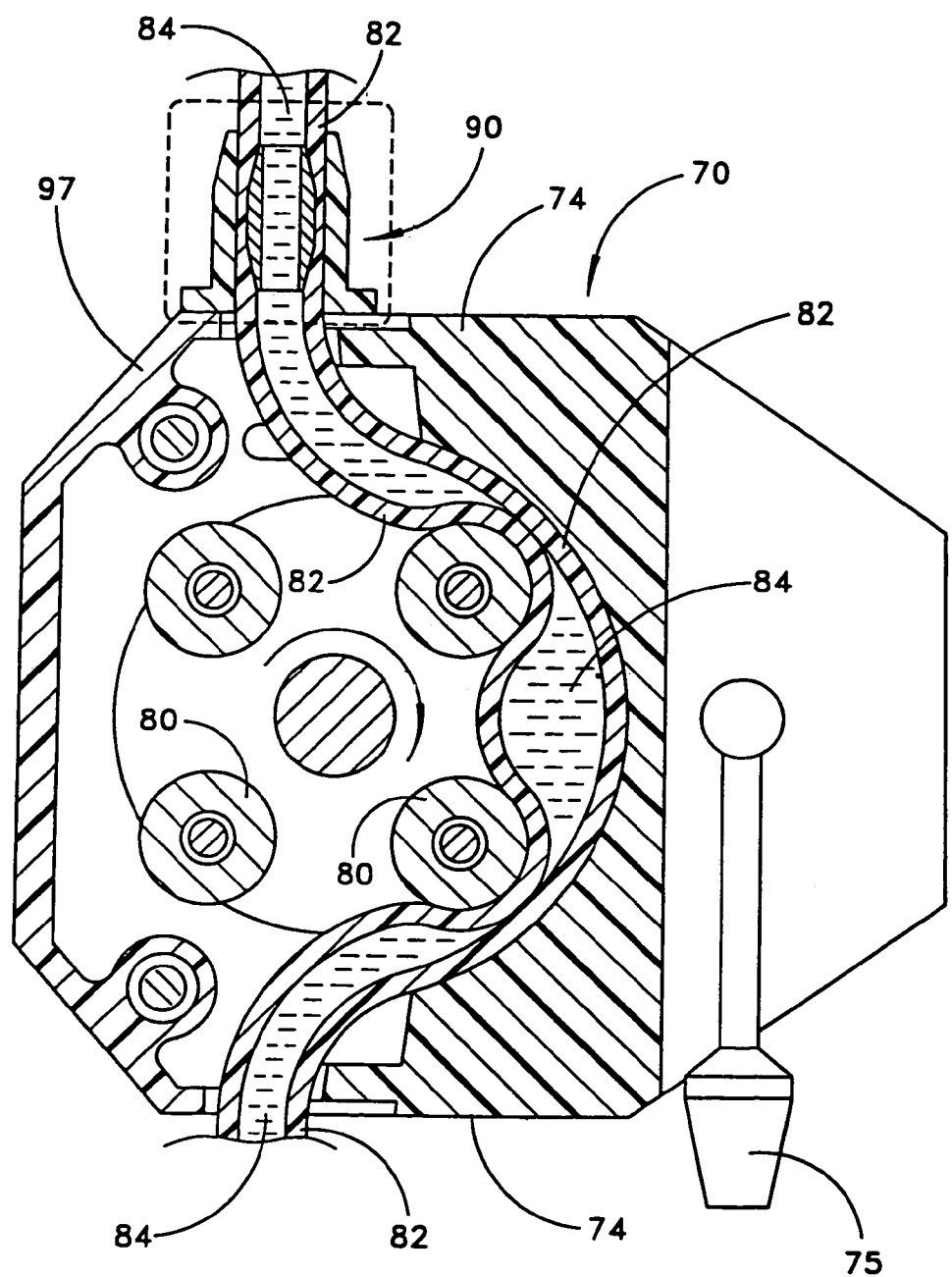
FIG. 5 is a cross-sectional view of one embodiment a roller pump in a closed position with fluid in the fluid line in a system incorporating features of the present invention.

The speed at which the pump 70 pumps the fluid is generally variable and controlled through the controller 60. In the preferred embodiment, the pump 70 comprises a peristaltic (roller) pump. An example of one embodiment of a peristaltic pump is shown in FIGS. 3–5. As shown in FIG. 3, a portion 82 of the fluid supply line 22 is passed through the pump 70 and around an outer edge of rollers 80. The tubing portion 82, also referred to herein as the tube or tubing 82, of the fluid supply line 22 is generally different from the remainder of the fluid supply line 22 and comprises a tube that has special mechanical properties that allow the tubing to be used within the roller portion of the fluid pump 70. In one embodiment, the tubing 82 can be made from Tygon® LFL tubing or a tubing with similar mechanical properties. One type of tubing suitable for use with peristaltic (roller) pump(s) is commercially available from the Plastron, a Tekni-Plex Co., City of Industry, Calif. In one embodiment, the length of the tubing 82 can be approximately 300 millimeters, although any suitable length can be used.

In FIG. 3, the pump handle 75 is in an upward position and the pump cover 74 is open. In the open position, the rollers 80 do not apply pressure to the tube 82. When the handle 75 is moved downward, or into a closed position as shown in FIGS. 4 and 5, the pump rollers 80 apply pressure, or squeeze the tube 82. As the pump motor rotates as shown in FIG. 5, the rollers 80 rotate and force fluid 84 in the tube 82 to be pumped through the fluid line 22. Although the fluid pump 70 shown in FIGS. 3–5 has four rollers, any suitable number of rollers 80 can be used to provide a desired, relatively steady fluid flow. In the preferred embodiment, the pump 70 has 6 rollers in order to reduce the amplitude of fluid pulsations in the fluid line 22. One example of a roller pump that can be used in one embodiment of the present invention is roller pump model number 900-1021 manufactured by the Barnant Company, Barrington, Ill. In the preferred embodiment of the invention, the roller pump can be powered by an electric motor model number 118752 and planetary gearhead model number 110396, commercially available from Maxon Precision Motors, Burlingame, Calif.

Referring to FIGS. 2–6, in one embodiment, a fluid supply line securing device 90 can be used to keep the tubing portion 82 of the fluid supply line from being pulled through the roller pump when the pump 70 is operating.

Figure 6:
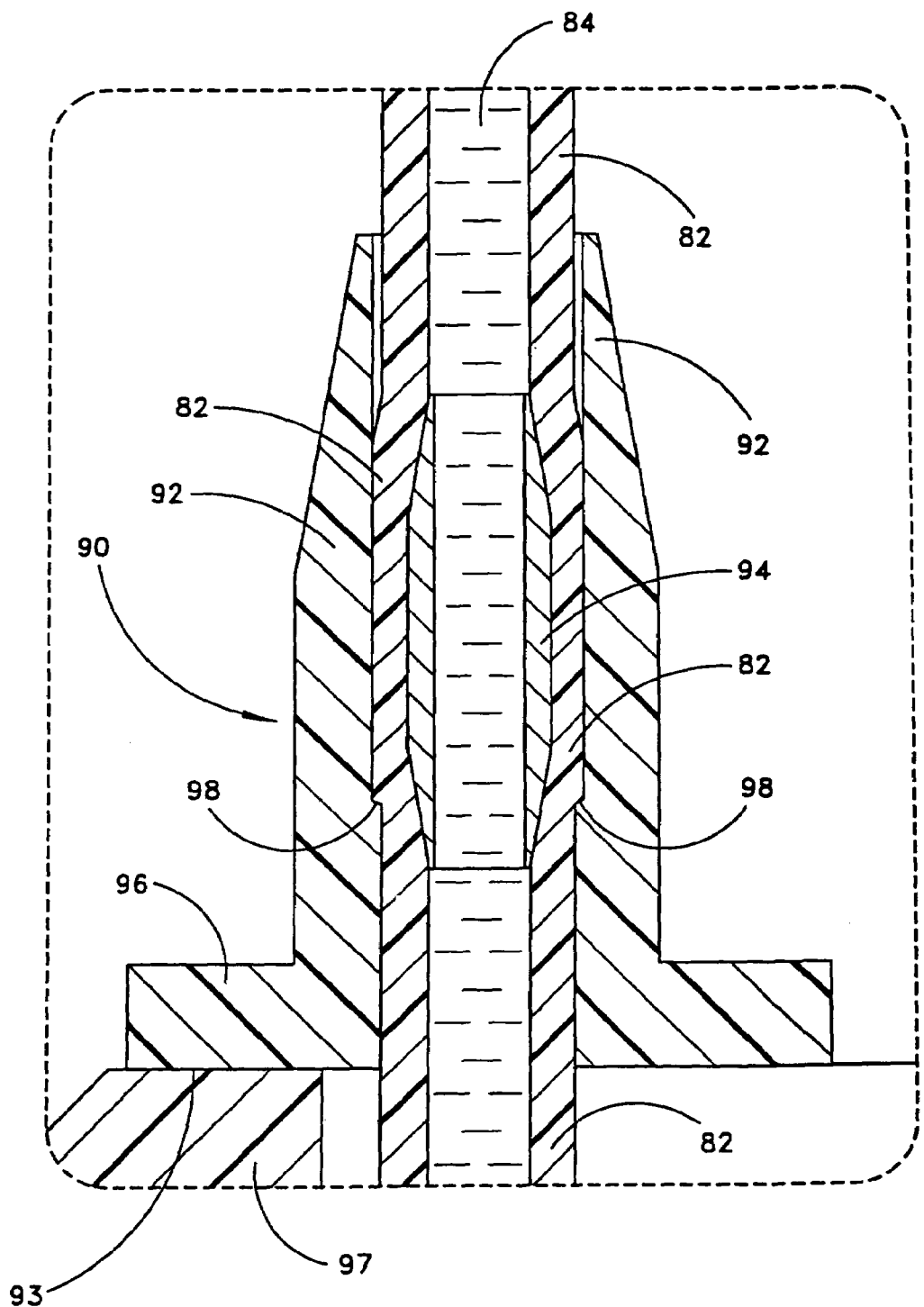
FIG. 6 is a cross-sectional view of one embodiment of a fluid supply line securing device incorporating features of the present invention.

As shown in FIG. 6, the fluid supply line securing device 90 generally comprises a receiving member 92 that at least partially surrounds tube 82 and prevents tube 82 from being pulled through the roller pump. The outer surface of the tube 82 can be bonded in any suitable manner, such as for example gluing, to an inner surface of a generally tubular channel of the receiving member 92.

Referring to FIG. 6, in one embodiment, a generally hollow sleeve 94 can be adapted to be inserted into a proximal portion of the tube 82. An outer diameter of the sleeve 94 is generally larger than an inner diameter of the tube 82 so that a portion of the tube 82 around the sleeve 94 is distended when the sleeve 94 is inserted into the tube 82. The portion of the tube 82 around the sleeve 94 becomes wedged against the shoulder 98 formed in the tubular channel of the receiving member 92 and prevents the proximal portion of the tube 82 from being pulled through the receiving member 92.

As shown in FIG. 6, appropriate placement of the tube 82 within the fluid pump 70 requires that a distal end section 96 of the receiving member 92 becomes abutted against a corresponding surface 93 of a fluid pump housing 97. This prevents the receiving member 92 and the tube 82 from being pulled through the fluid pump when the rollers 80 are rotating.

Although as shown in FIG. 2, the pump 70 is shown as integrated into the controller 60, it should be understood that the pump 70 could also be located externally to the controller 60, and comprise for example, a stand alone fluid pumping system. In an alternate embodiment, any suitable device for pumping fluid can be used, such as for example, a centrifugal pump or syringe type device. It is a feature of the present invention to be able to provide a variable and/or regulated flow of fluid through the inner lumen of elongated tube 28 during the operation of the system 10.

As shown in FIG. 2, in one embodiment, the fluid supply system 50 can comprise a fluid bag connected to a drip chamber 52 that is connected to the fluid line 22. The fluid supply line 22 can generally comprise one or more sections of fluid supply tubing that can be coupled together in any suitable manner. As discussed above, in the preferred embodiment, the fluid supply line 22 includes a tubing portion 82 that has special mechanical properties suitable for use with a peristaltic (roller) pump. Preferably, the tubing portion 82 is not only made from a material that has special mechanical properties different from the rest of the fluid supply line 22, but also has inner and/or outer diameters that are different from the inner and/or outer diameters of the rest of the fluid supply line 22.

Figure 26:
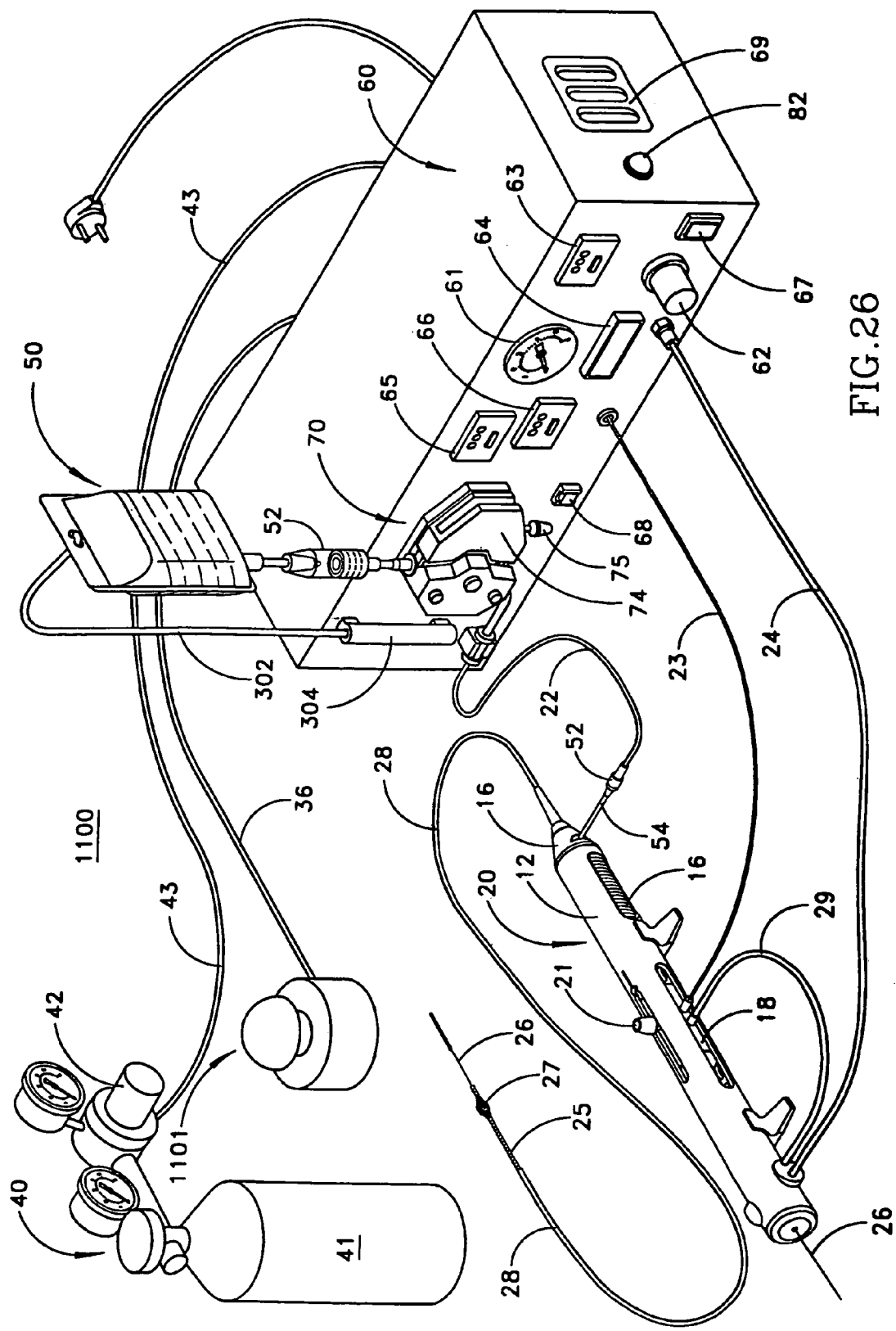
FIG. 26 is a perspective view of one embodiment of a system incorporating features of the present invention.

The system 10 also includes the activation device 30 that is coupled to the controller 60 via control line or lines 36. Although as shown in FIG. 2, line 36 is a single line, it should be understood that in the preferred embodiment, the line 36 comprises a cable that includes one or more electrical or fiberoptic lines 36. In an alternate embodiment, the line 36 could include pneumatic or other suitable types of communication lines. The activation device 30 is generally adapted to control or activate an increased flow rate of fluid from or through the pump 70. The activation device 30 can also be used to control the activation of the gas turbine of the RAD. Generally, the activation device 30 is a switching device having "ON" and "OFF" positions. In one embodiment as shown in FIG. 2, the activation device 30 comprises a pair of pedal switches, a pump pedal 32 and a turbine pedal 34. In a preferred embodiment, pedal switches 32 and 34 are electrical switches and control line 36 comprises an electrical cable with more than one wire therein, each wire adapted to carry electrical or communication signals. It is a feature of the present invention to allow an operator of the RAD 20 to increase the speed of the pump 70 or activate the gas turbine using the foot pedals 32 and 34 shown in FIG. 2, or a single foot switch 1101 as shown in FIG. 26.

Figure 25:
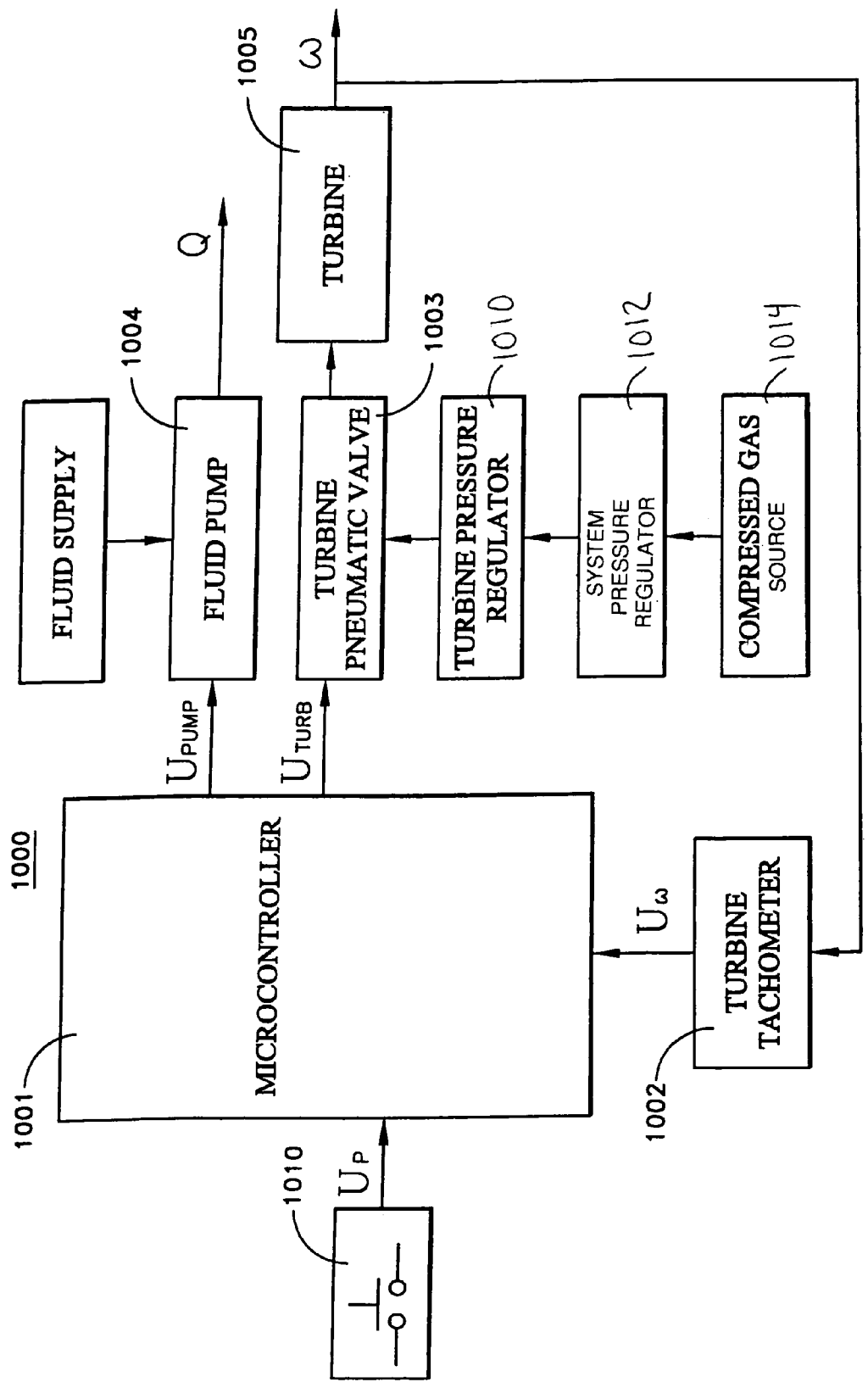
FIG. 25 is a block diagram of one embodiment of a control system for a system incorporating features of the present invention.

In an alternate embodiment any suitable switching or control device can be used other than a pedal activated switch to provide an "ON" or "OFF" activation signal. For example, as shown in FIGS. 25 and 26, a single pedal switch 1010 or 1101 and control systems 1000 or 1100, may be utilized in such a fashion so that a first activation of the switch (the first pulse or the first control signal) causes the fluid pump 70 to increase its speed of rotation, then the second activation of the switch (the second pulse or the second control signal) causes the fluid pump 70 to continue to rotate at the increased speed and activates the gas turbine, and finally, the third activation of the switch (the third pulse or the third control signal) turns off both the gas turbine and (after a delay if needed) the fluid pump 70, bringing the entire system to its "steady-state" or "static" mode. For example, in such static mode the fluid pump 70 returns to it minimum or "min" fluid flow rate and the gas turbine is turned "OFF.".

The controller 60 shown in FIG. 2 is generally adapted to control and monitor the operations of the system 10, including the fluid flow rate and gas turbine function and speed. The controller 60 can include displays 61, 63, 64, 65 and 66 to monitor compressed gas pressure applied to the gas turbine of the RAD, turbine rotational speed, various procedure time intervals, and other functions of the system 10, controls and switches 62, 67 and 68 to operate the various functions of the system 10 as well as connections to each of the components of the system 10. The controller 60 will also include the electronics and circuitry needed to operate the system 10.

For example, as shown in FIG. 2, display 65 can comprise an "individual" event timer adapted to display and/or record the length of time during which the turbine was rotating after each individual activation ("individual event time"). Display 66 can comprise a "procedure timer" that displays the sum of the individual event times, i.e. the total time during which the gas turbine was operational throughout the angioplasty procedure. Each of the displays can include a reset button to reset the time. For example, the "procedure timer" may be used to record a total time used to completely open the stenotic lesion and then reset back to "zero." Display 63 can be used to display a rotational speed of the turbine 19. In an alternate embodiment, any suitable number or types of displays can be used for indicating the functions and events of the system 10.

Figure 7:
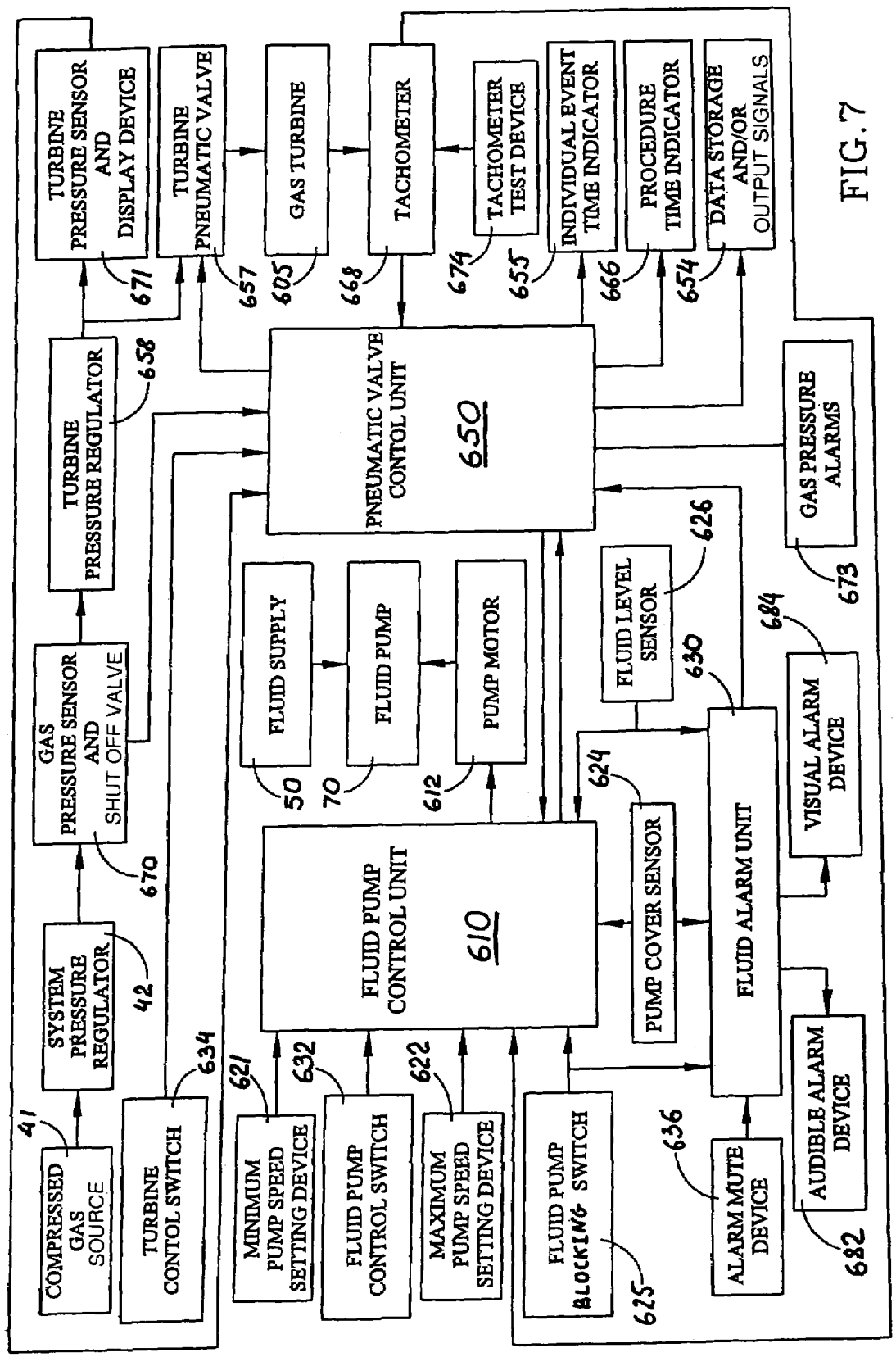
FIG. 7 is a block diagram illustrating one embodiment of the functional aspects of a controller for a system incorporating features of the present invention.

Referring to FIG. 7, a block diagram illustrating the functional aspects of one embodiment of the controller 60 is shown. With reference to FIGS. 2 and 7, the controller 60 can be used to control the activation and speed of the pump 70, the activation and speed of the gas turbine of the RAD and, for these purposes, can include a fluid pump control unit 610 and a pneumatic valve control unit 650.

Figure 13:
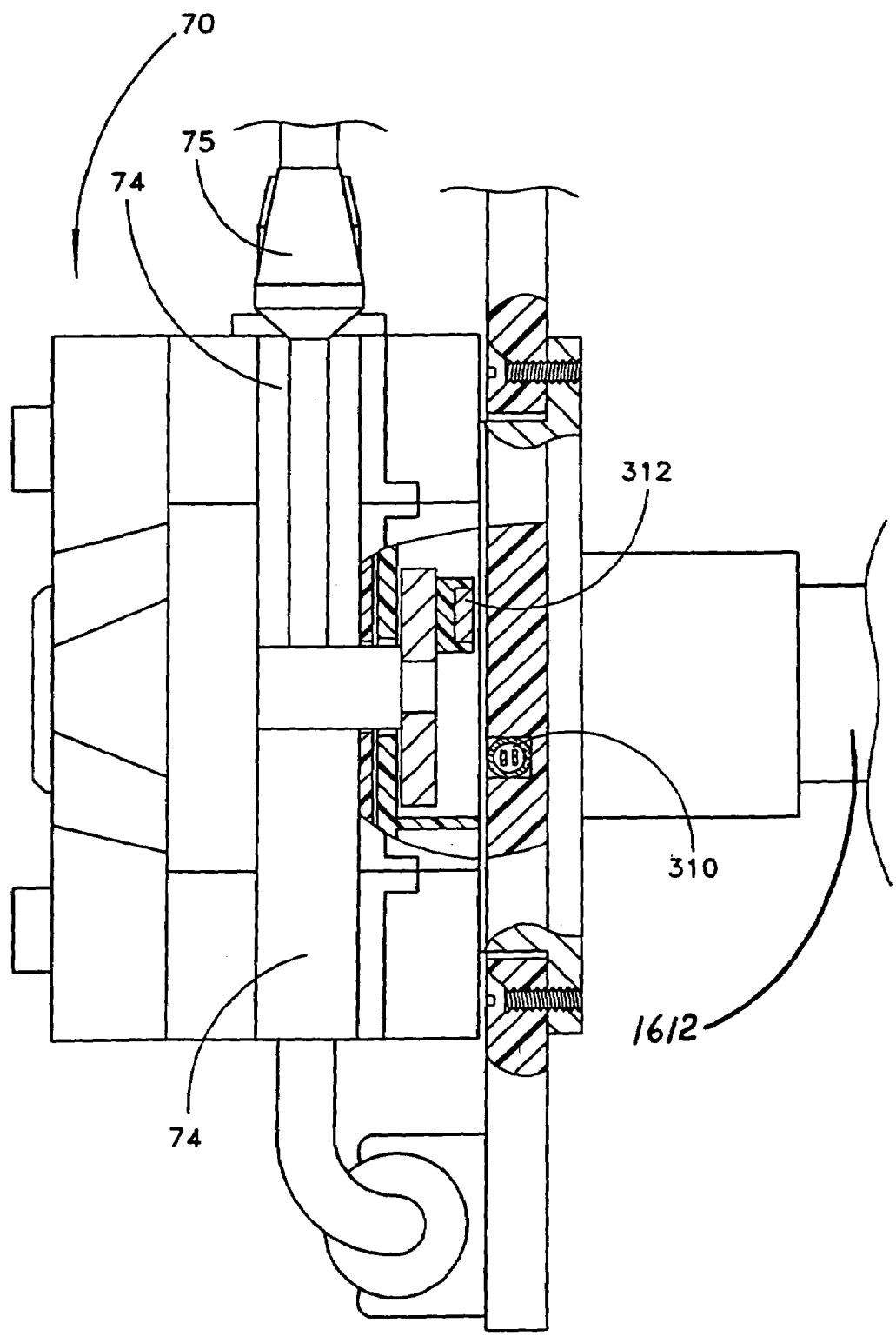
FIGS. 13 and 14 are partial cross-sectional views of a pump cover sensor in embodiments of systems incorporating features of the present invention.
Figure 14:
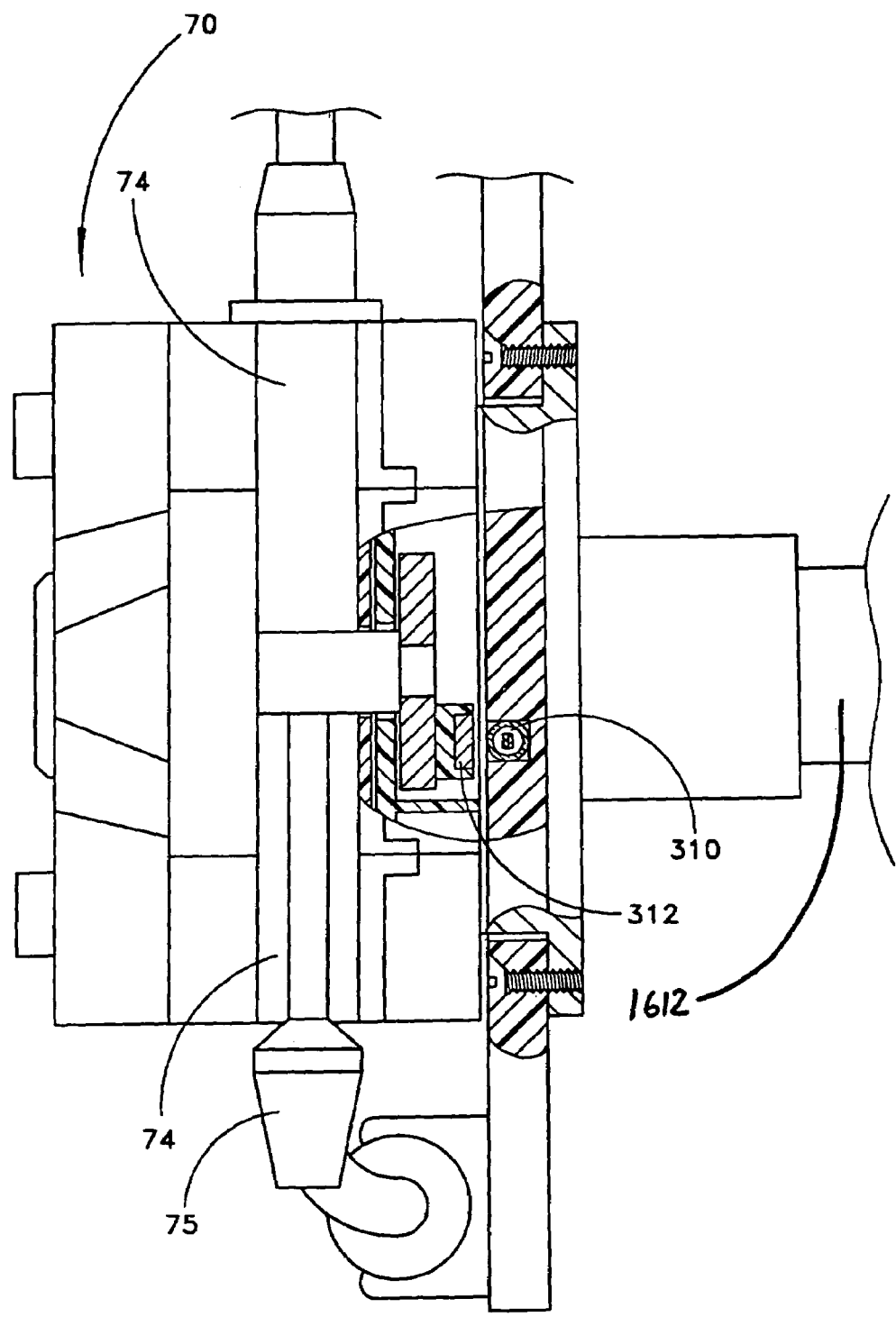

The pump control unit 610 is generally adapted to control the speed of a fluid pump motor 612 in order to regulate the flow rate of fluid through the inner lumen of the, catheter 28. The fluid pump motor 612 is also shown in FIGS. 13 and 14 as a fluid pump motor 1612. The controller 60 can include a minimum pump speed setting control or device 621, which can be adjusted to set the minimum fluid flow rate or speed of the pump motor 612 when the gas turbine and the drive shaft 25 of the RAD are not rotating, for example. The maximum pump speed setting control or device 622 can be adjusted to set a maximum fluid flow rate, or the maximum speed of the pump motor 612.

When electric power is applied to the controller 60, the pump control unit 610 can set the pump motor 612 to operate in a "steady-state" or "static" mode. In this static mode the gas turbine and the drive shaft 25 are generally not rotating and minimal flow rate of fluid is maintained. When, for example, the fluid pump control switch 632 (which is similar to pedal switch 32 in FIG. 2) is activated, the pump control unit 610 can send a signal to the pump motor 612 to increase its speed. The increase of the speed of the pump motor 612 will increase the fluid flow rate.

The pneumatic valve control unit 650 generally controls the operation of the gas turbine 605 of the RAD. When the turbine control switch 634 (similar to pedal switch 34 in FIG. 2) is activated the pneumatic valve control unit 650 sends a signal to activate the turbine pneumatic valve 657, which allows compressed gas from the turbine pressure regulator 658 to be applied to the gas turbine 605 of the RAD. The fluid pump control unit 610 also communicates with the pneumatic valve control unit 650 to coordinate operation of the fluid pump 70 with the gas turbine of the RAD. It is a feature of the present invention that the turbine control switch 634 needs to be activated within a predetermined time period after the fluid pump control switch 632 is deactivated in order to activate the gas turbine of the RAD. If the turbine control switch 634 is not activated within the predetermined time period after deactivation of the fluid control switch 632, operation of the gas turbine of the RAD can be either prevented or delayed. In one embodiment, when the turbine control switch 634 is activated before activation of the pump control switch 632, of after the expiration of the predetermined time period, operation of the gas turbine of the RAD will be delayed for another predetermined time period after activation of turbine control switch 634 during which time the fluid pump 70 is pumping fluid at an increased or maximum speed.

The turbine pressure regulator 658 could comprise a Precision Low Pressure Regulator, Type LPR-1/4-4, commercially available from FESTO Corporation, Hauppauge, N.Y. The turbine pneumatic valve 657 could comprise a single solenoid valve type MFM-5-1/8-S-B, also available from the FESTO Corporation.

Compressed gas pressure at the output of the turbine pressure regulator 658 is measured and displayed by the turbine pressure sensor and display device 671, (which is similar to the turbine pressure display device 61 in FIG. 2). Both turbine pressure sensor 671 and turbine tachometer 668 may be in communication with the pneumatic valve control unit 650, which may be programmed to turn off or deactivate the turbine pneumatic valve 657 if a discrepancy of predetermined magnitude develops between pressure applied to the gas turbine 605 and the rotational speed of the turbine.

When the gas turbine of the RAD is activated, the controller 60 can include an "individual" event time indicator 655 (display 65 in FIG. 2) that indicates the length of time during which the turbine was rotating after each individual activation. A "procedure" time indicator 666 (display 66 in FIG. 2) can be used to display a total time during which the gas turbine was operational throughout the angioplasty procedure or part thereof.

The pneumatic valve control unit 650 could also provide data storage and/or output signal(s) 654 that could be used to plot the operation of the gas turbine and other components of the system 10. For example, the data storage and/or output signal(s) 654 could be fed to a logger or chart recorder in order to plot the time and functions of the gas turbine 605, fluid pump 70 and other elements of the controller 60, such as for example, gas pressure applied to the gas turbine and its rotational speed, under such pressure, may be logged.

During a rotational angioplasty procedure a fluid such as saline is pumped from the fluid supply 50 through the elongated tube 28. When the gas turbine of the RAD is activated the drive shaft 25 is rotated at a high speed. The turbine block 18 can be moved forward and/or backward with respect to the housing 12 of the RAD 20 thereby allowing the operator to move the drive shaft 25 and its abrasive element 27 forward and/or backward across the stenotic lesion. Generally, in the present invention, when the drive shaft 25 is rotating, saline is being pumped from or through the pump 70 at a higher rate of flow than when the drive shaft 25 is not rotating. The increased flow of saline can provide, among other things, enhanced cooling of the treated area and substantially uninterrupted flushing away of the small particles generated as the stenotic material is removed by the abrasive element 27. Saline is pumped through the elongated tube 28 at a minimal flow rate when the system 10 is in a static state and the drive shaft 25 is not rotating.

Figure 8:
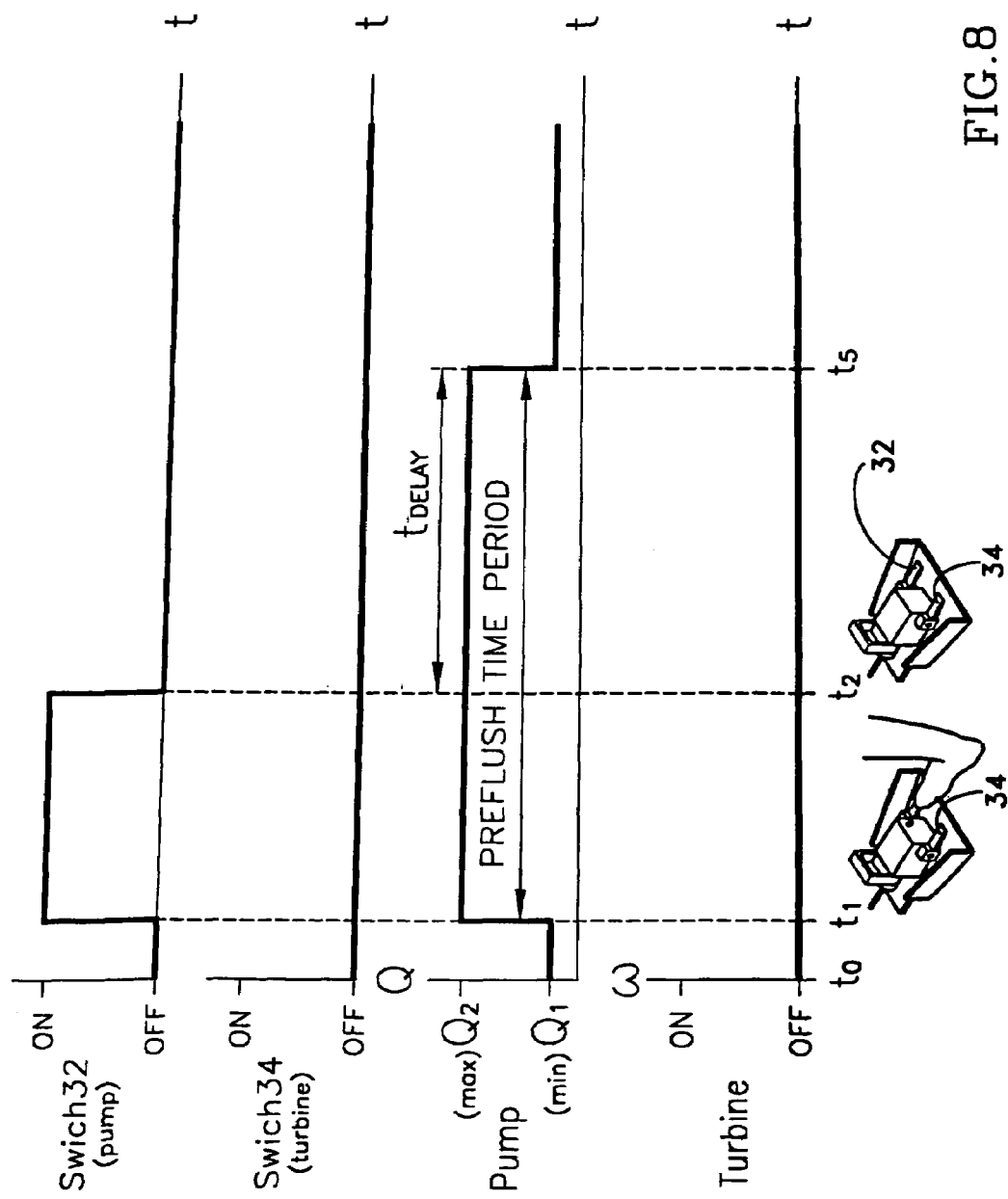
FIG. 8 is a timing diagram for pump and turbine activation periods in one embodiment of a system incorporating features of the present invention.

In the present invention, the controller 60 and the activation device 30 are adapted to "delay" activation of the gas turbine of the RAD to provide a "preflush" of saline prior to initiating "active" rotation of the gas turbine. The term "preflush" as used herein describes pumping of saline through the elongated tube 28 at an increased flow rate. For example, referring to FIG. 8, at time $t_o$, the gas turbine, represented by its rotational speed $\omega$, is off, and the saline flow rate Q is at flow rate $Q_1$. In one embodiment flow rate $Q_1$ could be at a minimum or "min" level when the system 10 is in a static mode. Upon activation of switch 32, the saline flow rate Q increases from flow rate $Q_1$ to $Q_2$. Saline flow rate $Q_2$ is a higher flow rate than $Q_1$, being for example, a maximum or "max" flow rate. The gas turbine remains off. It should be understood that although the saline flow rate $Q_2$ is shown as increasing to the "max" upon activation of pedal switch 32, any suitable flow rate $Q_2$ can be used. At time $t_2$, the pedal switch 32 is deactivated, or is "OFF." The saline flow rate remains at increased flow rate $Q_2$ for a period of time shown as $t_{delay}$. In FIG. 8 this $t_{delay}$ time period corresponds to the time period between $t_2$ and $t_5$. A period of time between $t_1$ and $t_2$, together with that period of time within $t_{delay}$ during which saline flow is maintained at an increased flow rate prior to activation of the gas turbine, is referred to herein as the "preflush time period." The drive shaft 25 and its abrasive element 27 are not rotating during the preflush time period.

The preflush time period prior to activation of the drive shaft 25 provides several advantages. Some of these advantages can include for example, flushing both the abrasive element 27 and the stenotic area to be treated with saline that can include a suitable concentration of heparin and other pharmaceuticals that can prevent platelet aggregation and thrombus formation. The dilution of the blood that flows through the area of treatment and around the abrasive element may be sufficient to significantly reduce the potential for platelet activation, platelet aggregation and thrombus formation. Dilution or even hydrolic occlusion of blood flow through the area of treatment may also reduce the number of red blood cells in the treatment area and or around the abrasive element 27 of the drive shaft 25, and, therefore, prevent hemolysis of the red blood cells at the time when the drive shaft 25 and its abrasive element 27 begin and continue to rotate. In general, the "preflush" flow of fluid to the site of the tissue removal prior to the turbine activation provides a more favorable environment for the rotational angioplasty procedure.

Figure 9:
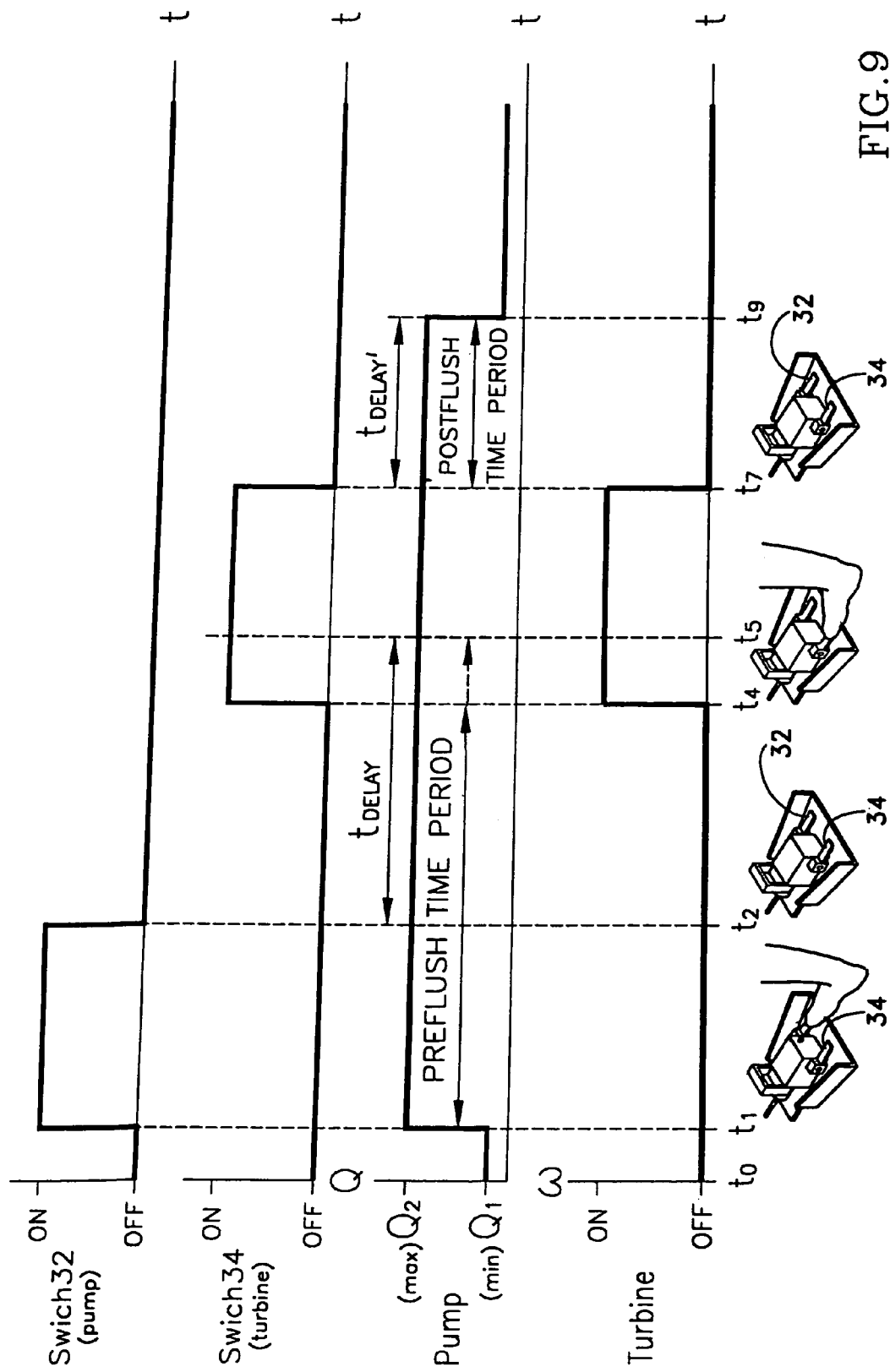
FIG. 9 is a timing diagram illustrating pump and turbine activation periods in one embodiment of a system incorporating features of the present invention.

It is a feature of the present invention to provide a preflush time period so that activation of the gas turbine of the RAD is prevented or precluded without a continuous preflush time period. In the present invention, the acceleration of the saline flow rate is substantially independent from rotation of the gas turbine and drive shaft 25 of the RAD 20. For example, referring to FIG. 9, at time $t_4$, the turbine pedal switch 34 is activated or is "ON." This activation of switch 34 instructs the controller 60 to activate the gas turbine of the RAD 20 and initiate rotation of the gas turbine and drive shaft 25. Since the activation of switch 34 occurs at time $t_4$ and within the time period $t_{delay}$, the gas turbine of the RAD is activated. As shown in FIG. 9, the saline flow rate Q remains at increased flow rate $Q_2$ during at least the time period $t_4$ to $t_7$ when the gas turbine is "ON" or rotating.

Figure 10:
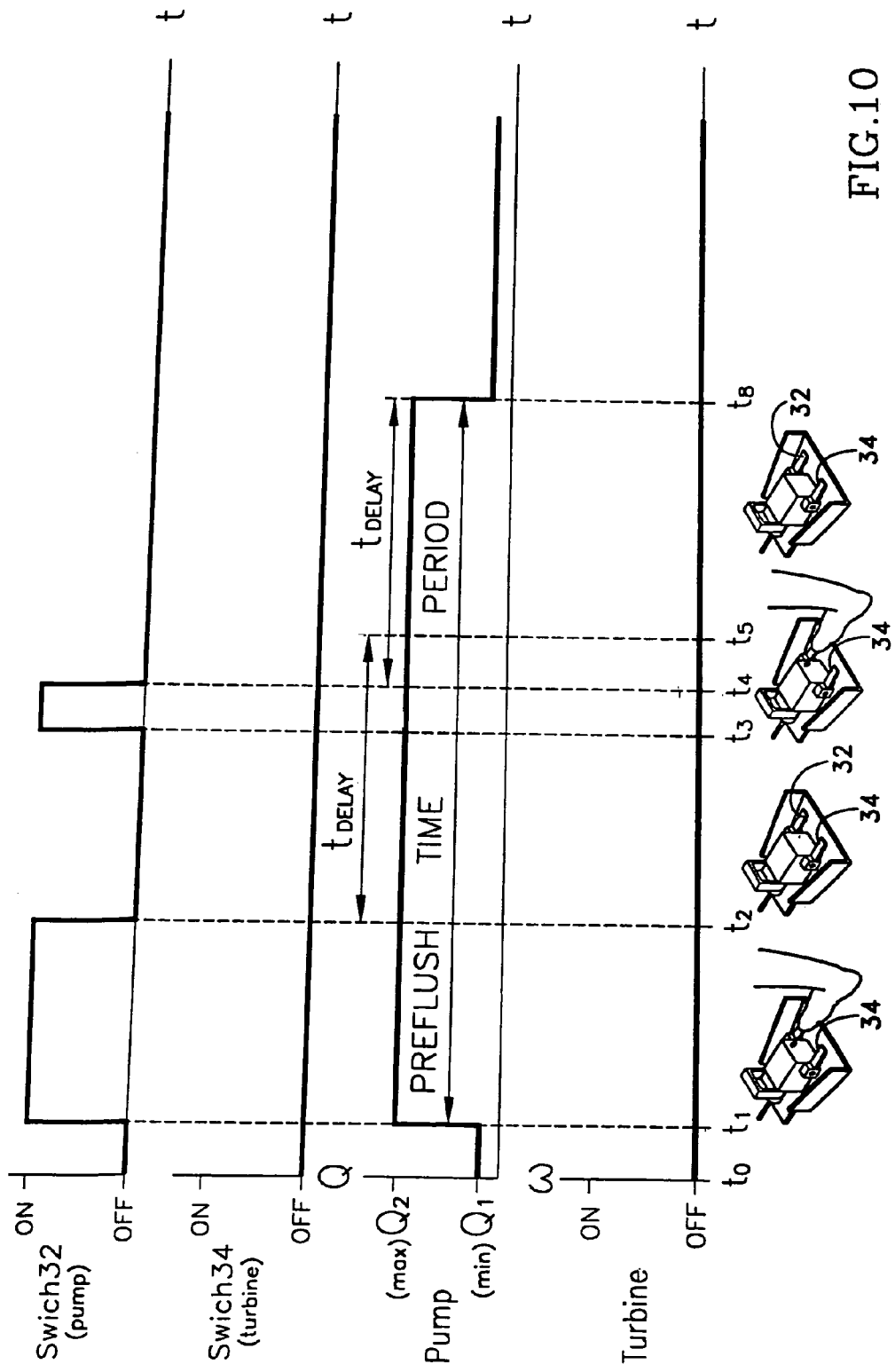
FIG. 10 is a timing diagram of pump and turbine activation periods in one embodiment of a system incorporating features of the present invention.

Referring to FIG. 10, the $t_{delay}$ time period can be extended or repeated by reactivating the fluid pump pedal switch 32. For example, at time $t_o$, the gas turbine is "OFF" and the fluid flow rate is at $Q_1$. At time $t_1$, fluid pump pedal switch 32 is activated, which, as shown in FIG. 10, is represented as a depression of pump pedal switch 32.

Activation of the fluid pump switch 32 causes the saline flow rate Q to increase from $Q_1$ to $Q_2$. At time $t_2$, pump pedal switch 32 is released or deactivated and the fluid flow remains at increased flow rate $Q_2$. The saline flow rate shall remain at increased saline flow rate $Q_2$ for the $t_{delay}$ period, shown as from time $t_2$ to time $t_5$. As shown in FIG. 10, at the time $t_3$ (before the end of the time period $t_{delay}$) fluid pump pedal switch 32 has been activated for a time period $t_3$ to $t_4$. At the time $t_4$, when the fluid pump pedal switch 32 is deactivated, the time period $t_{delay}$ starts again, running from time $t_4$ to $t_8$. It is a feature of the present invention that this "preflush" or preflush time period can be executed or extended as many times as desired by the operator of the system 10.

Referring to FIG. 9, if the turbine pedal switch 34 is activated during the $t_{delay}$ time period, the gas turbine switches "ON." For example, as shown in FIG. 9, at time $t_2$, the fluid pump pedal switch 32 is deactivated and the $t_{delay}$ time period starts, with the fluid flow rate remaining at the increased flow rate $Q_2$. At time $t_4$, or before the time period $t_{delay}$ has expired, the turbine pedal switch 34 is activated. The gas turbine goes from "OFF" to "ON" and the saline flow rate remains at the increased flow rate $Q_2$. At time $t_7$ the gas turbine is switched "OFF" by the release of turbine pedal switch 34. In one embodiment, as shown in FIG. 9, the saline flow rate Q can remain at the increased level $Q_2$ for another delay time period from time $t_7$ to time $t_9$ as represented by $t_{delay''}$. In an alternate embodiment, the fluid flow rate could go from $Q_2$ to $Q_1$ at time $t_7$. It is a feature of the present invention to provide a "postflush" or "postflush time period" of accelerated or increased fluid flow rate after the gas turbine and drive shaft 25 stop rotating. The time period for $t_{delay}$ or $t_{delay'}$ can be any suitable or desired time period. The $t_{delay}$ and $t_{delay'}$ time periods may comprise time periods of different length.

Figure 11:
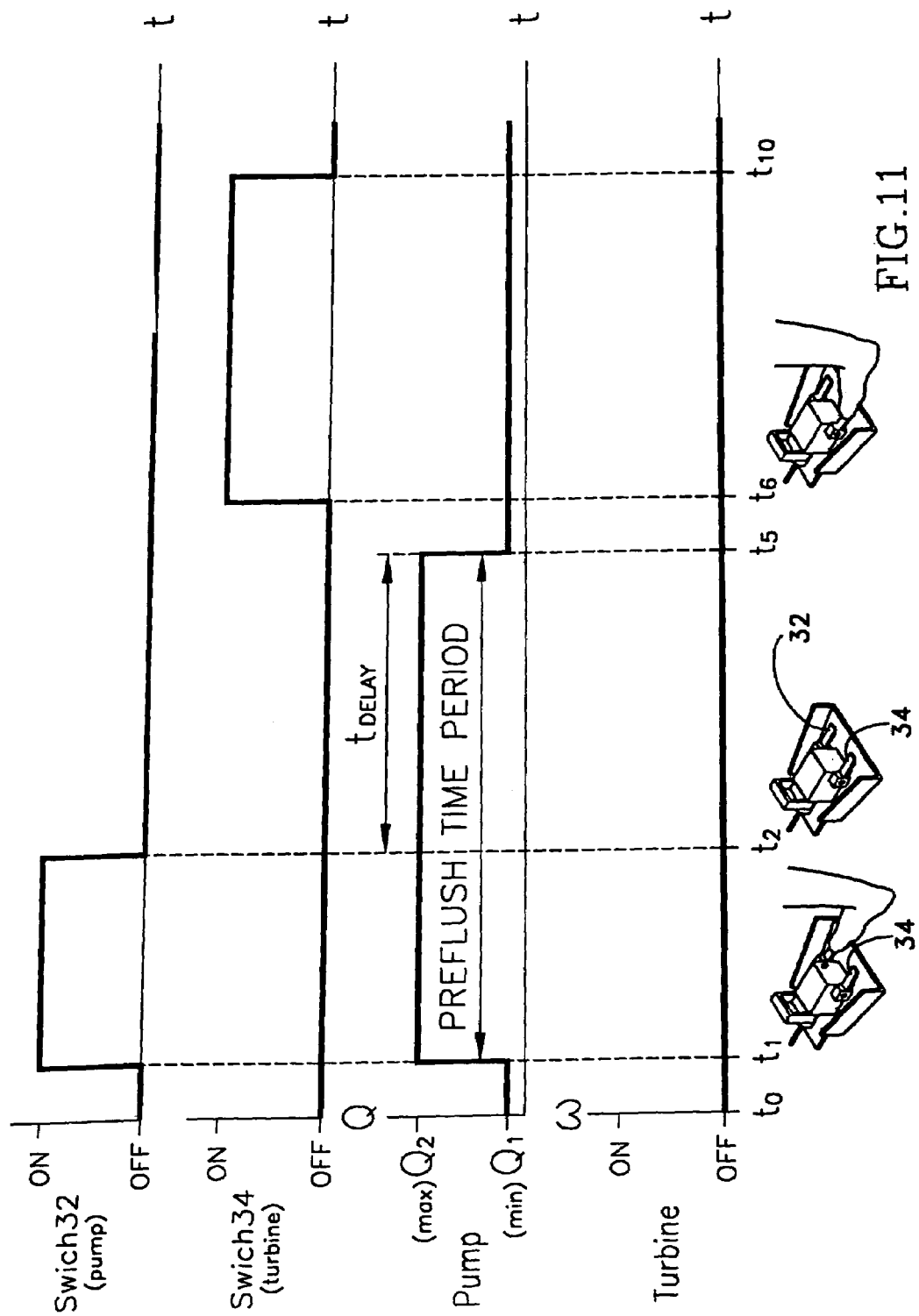
FIG. 11 is a timing diagram of pump and turbine activation periods in one embodiment of a system incorporating features of the present invention.

Referring to FIG. 11, if the turbine pedal switch 34 is activated at any time $t_6$ after the time period $t_{delay}$ has expired at the time $t_5$, then the controller 60 could prevent the turbine from activating. If the gas turbine of the RAD 20 has not been activated during an uninterrupted preflush time period as shown in FIG. 11, then the controller 60 may also be designed or programmed to switch the fluid pump 70 into the "preflush" mode upon activation of the turbine pedal switch 34 and activate the gas turbine of the RAD 20 only after a predetermined preflush time period has expired. It is a feature of the present invention to provide an increased level of fluid flow through an elongated tube 28, and around the drive shaft and through the stenotic treatment area prior to rotation of the drive shaft 25.

The fluid pump 70 is not powered by or brought into motion by the gas turbine or any other prime mover of the RAD and therefore an acceleration of the fluid flow around the driveshaft 25 is only modestly affected by the rapid rotation of the drive shaft, which when rapidly rotated can act as a screw pump. In the preferred embodiment the rapid rotation of the drive shaft 25 causes about a 30% decrease in accelerated fluid flow rate when compared to accelerated fluid flow rate around a non-rotating drive shaft.

Figure 12A:
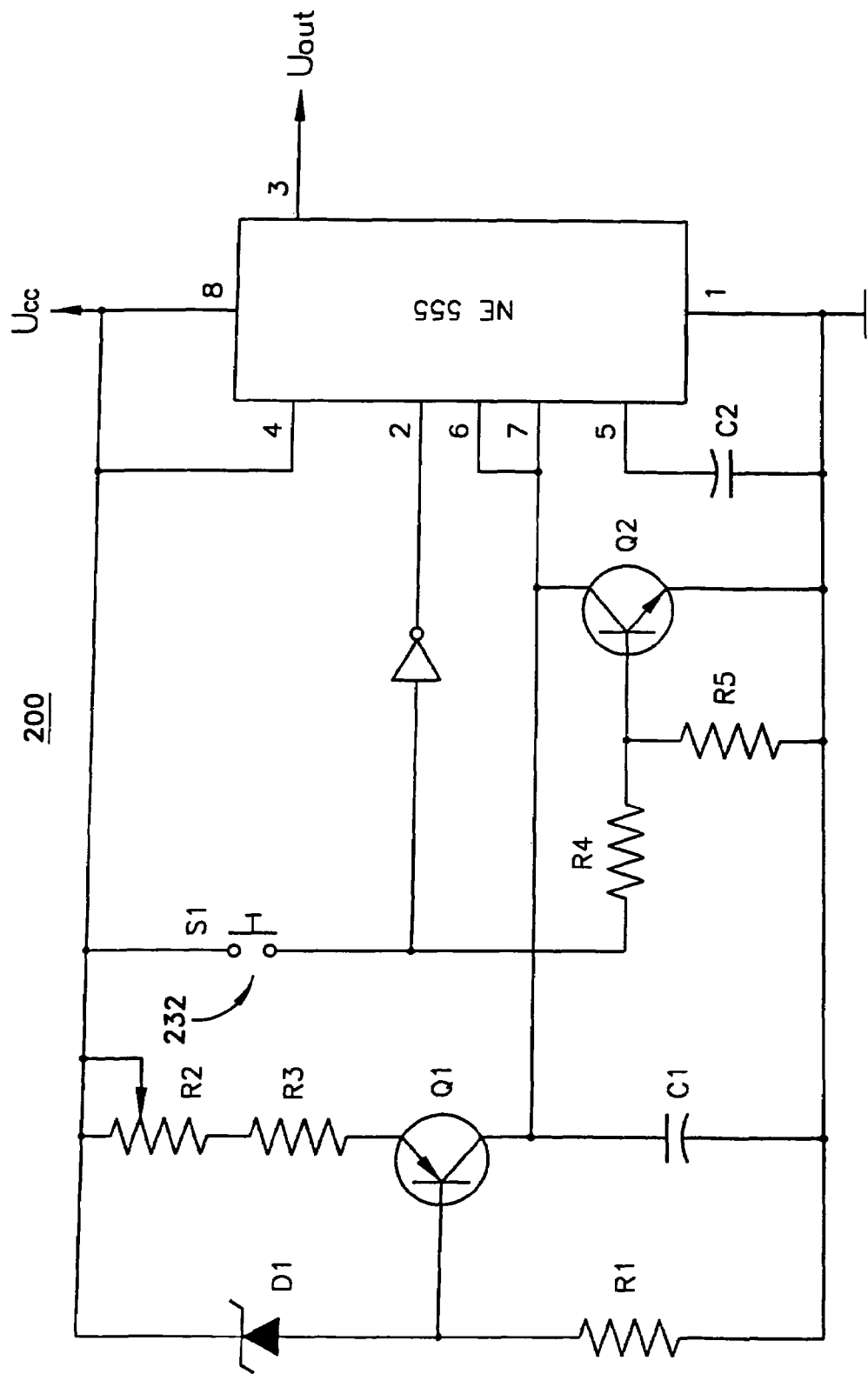
FIG. 12A a schematic diagram of one embodiment of a timing circuit to produce a delayed time period feature a system incorporating features of the present invention.

Referring to FIG. 12A, a timing circuit 200 could be used to provide the $t_{delay}$ time period after deactivation of the pump pedal switch 32 in the embodiment(s) of the invention shown in FIG. 2 and FIGS. 7–11.

Switch 232 of the timing circuit 200 remains "open" for as long as the pump pedal switch 32 is not activated. During that time period voltage across the capacitor $C_1$ is equal to the voltage across capacitor $C_2$ (voltages at inputs 5 and 7 of the Digital Circuit NE 555 are equal) and a control signal $U_{out}$ is 0 (zero). Activation of pedal switch 32 at the time $t_1$ in FIG. 8, for example, will "close" switch 232 thereby causing immediate discharge of the capacitor $C_1$ through the transistor $Q_2$. The control signal $U_{out}$ of the Digital Circuit NE 555 will immediately change from 0 to 1.

At the time $t_2$ in FIG. 8, for example, when the fluid pump pedal 32 is released and switch 232 opens, the capacitor $C_1$ charges and the Digital Circuit NE 555 provides control signal $U_{out}$ equal to 1 until the capacitor $C_1$ is fully charged. Therefore the fluid pump 70 continues to pump fluid at an accelerated or increased fluid flow rate only for as long as the control signal $U_{out}$ remains at 1.

At the time $t_5$ in FIG. 8, when the capacitor $C_1$ of the timing circuit 200 becomes fully charged (voltages at the inputs 7 and 5 become equal), the control signal $U_{out}$ will change from 1 to 0, thereby causing the fluid pump 70 to return to pumping fluid at the minimum or "min" fluid flow rate.

The $t_{delay}$ time period shown in FIGS. 8–11 is defined by a charge time of the capacitor $C_1$, in the timing circuit 200. The charge time of the capacitor $C_1$, and the $t_{delay}$ time period shown in FIGS. 8–11 may be adjusted within certain limits by the potentiometer $R_2$ in the timing circuit 200.

A separate timing circuit similar to the timing circuit 200 can be used with the turbine pedal switch 34 in order to provide the $t_{delay'}$ time period and "postflush" of accelerated flow of fluid after the turbine pedal switch 34 is released.

Figure 12B:
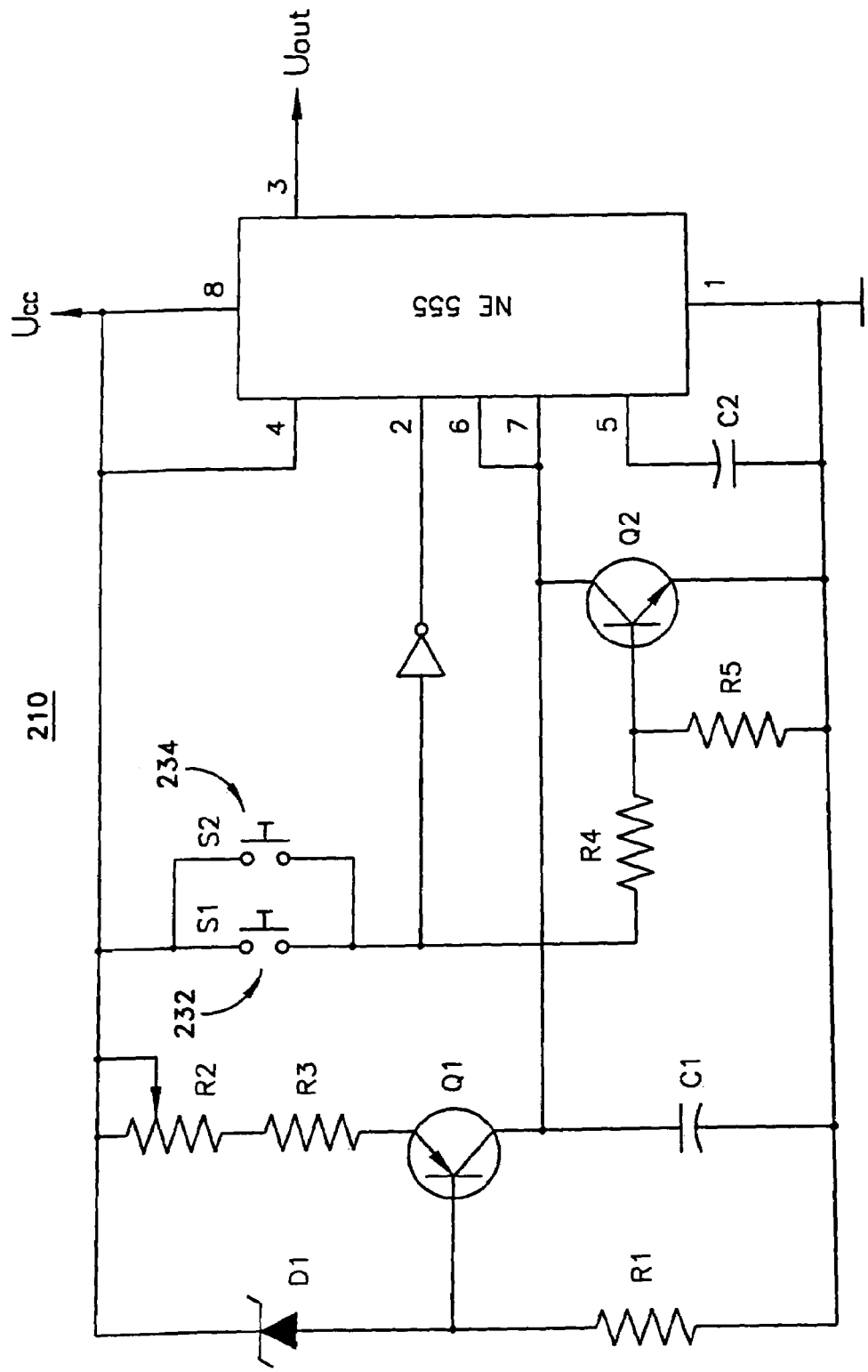
FIG. 12B a schematic diagram of one embodiment of a timing circuit to produce a delayed time period in a system incorporating features of the present invention.

As shown in FIG. 12B a single timing circuit 210 may provide equal $t_{delay}$ and $t_{delay'}$ time periods. This is accomplished by connecting in parallel switches 232 and 234, which correspond to pedal switches 32 and 34 in FIG. 2 and FIGS. 8–11.

The controller 60 could also include one or more safety devices to monitor proper operation of the system 10. For example, in one embodiment as shown in FIG. 7, the controller 60 could include a pump cover sensor 624. The pump cover sensor 624 could indicate whether the pump cover 74 shown in FIG. 2 is in an open or closed position. For example, as shown in FIG. 4, when the pump handle 75 is in a "DOWN" position, the pump cover sensor 624 can provide the pump control unit 610 with a suitable signal which allows the pump control unit 610 to activate the pump motor 612. If the pump cover 74 is "OPEN", as indicated by the pump cover handle 75 being in an "UP" position as shown in FIG. 3, pump cover sensor 624 will either not provide the signal that is needed to activate the pump motor 612 or can generate a signal that prevents the pump motor from being activated. Therefore, when the pump cover 74 is "OPEN", operation of the pump motor 612 can be prevented or interrupted.

In one embodiment as shown in FIGS. 13 and 14 the pump cover sensor 624 could comprise a switch device 310 adapted to detect a closed or open position of the pump cover 74. For example, as shown in FIG. 13 when the pump handle 75 is an "UP" position, the pump cover 74 is in an "OPEN" position. In FIG. 14 when the pump handle 75 is "DOWN", the pump cover 74 is "CLOSED." In the preferred embodiment, the switch 310 could comprise a magnetically operated sealed switch that uses a magnet 312 to preferably determine a "CLOSED" position of the pump cover 74. Such a switch, also called a reed switch, is commercially available from Premier Farnell plc of Chicago, Ill. In an alternate embodiment, any suitable device or switch can be used to determine an "OPEN" or "CLOSED" position of the pump cover 74, such as for example, a Hall effect switch, an optical switch, a mechanical switch or a limit switch.

As shown in FIG. 7, a fluid alarm unit 630 could be used to provide an audible and/or visual warning of the pump cover condition. For example, when the pump cover 74 is open, an audible alarm device 682 and/or a visual alarm device 684 can be activated to warn the user of the condition. An indicator 64 of the controller 60 shown in FIG. 2 could be used to display the visual warning. An audible alarm or verbal warning may be provided via siren or speaker 69 shown in FIG. 2.

As shown in FIG. 7 the controller 60 could also include a fluid level sensor 626. The fluid level sensor 626 could be used to detect a low level of fluid in the fluid supply system 50. The fluid level sensor 626 is in communication with both the fluid pump control unit 610 and the fluid alarm unit 630. If during an angioplasty procedure the fluid level in the saline bag 50 reaches a predetermined low level, then a fluid alarm unit 630 can activate visual and audible alarm devices 684 and 682 in order to warn or advice the operator of the system 10 of the condition. The controller 60 could also include an alarm mute device 636 that can allow the user to silence or mute the audible alarm device 682 for a predetermined period of time or a predetermined number of revolutions of the pump motor 612. Furthermore, in one embodiment of the invention, operation of the pump motor 612 and/or the gas turbine could be prevented or stopped if the fluid level sensor 626 detects a predetermined low level of fluid in the saline bag of the fluid supply 50. If the pump motor 612 is operating and the fluid sensor 626 detects a low fluid level, in one embodiment the fluid alarm unit 630 could activate the visual alarm device 684 and/or provide a verbal warning or activate audible alarm device 682 to indicate the situation to the user. The alarm mute device 636 can allow the user to silence the alarm 682 and continue the procedure. The visual alarm 684 could remain active. The controller 60 could also be adapted to reactivate the audible alarm 682 after it was silenced if a predetermined time period elapses or if the fluid pump 70 or pump motor makes a predetermined number of revolutions or if the fluid level reaches a next predetermined low level. This process could continue for as long as the operator desires or until a predetermined minimum level of fluid is reached. The controller 60 could also include a fluid pump blocking control switch 625, that when activated, could prevent operation of the fluid pump motor 612. Referring to FIG. 2, in one embodiment of the present invention, a push button 82 can be used to silence the audible alarm device 69 and push button 68 to operate the pump blocking control or device 625 shown in FIG. 7. In the preferred embodiment of the invention push button 68 comprises a pushbutton switch with a red screen. If an operator of the controller 60 activates push button 68 (prevents or stops operation of the fluid pump 70), then red screen of the pushbutton switch becomes illuminated by a filament or LED lamp.

The pushbutton switches of the type used in the preferred embodiment of this invention are commercially available from Apem Components, Inc. of Wakefield, Mass.

Figure 15:
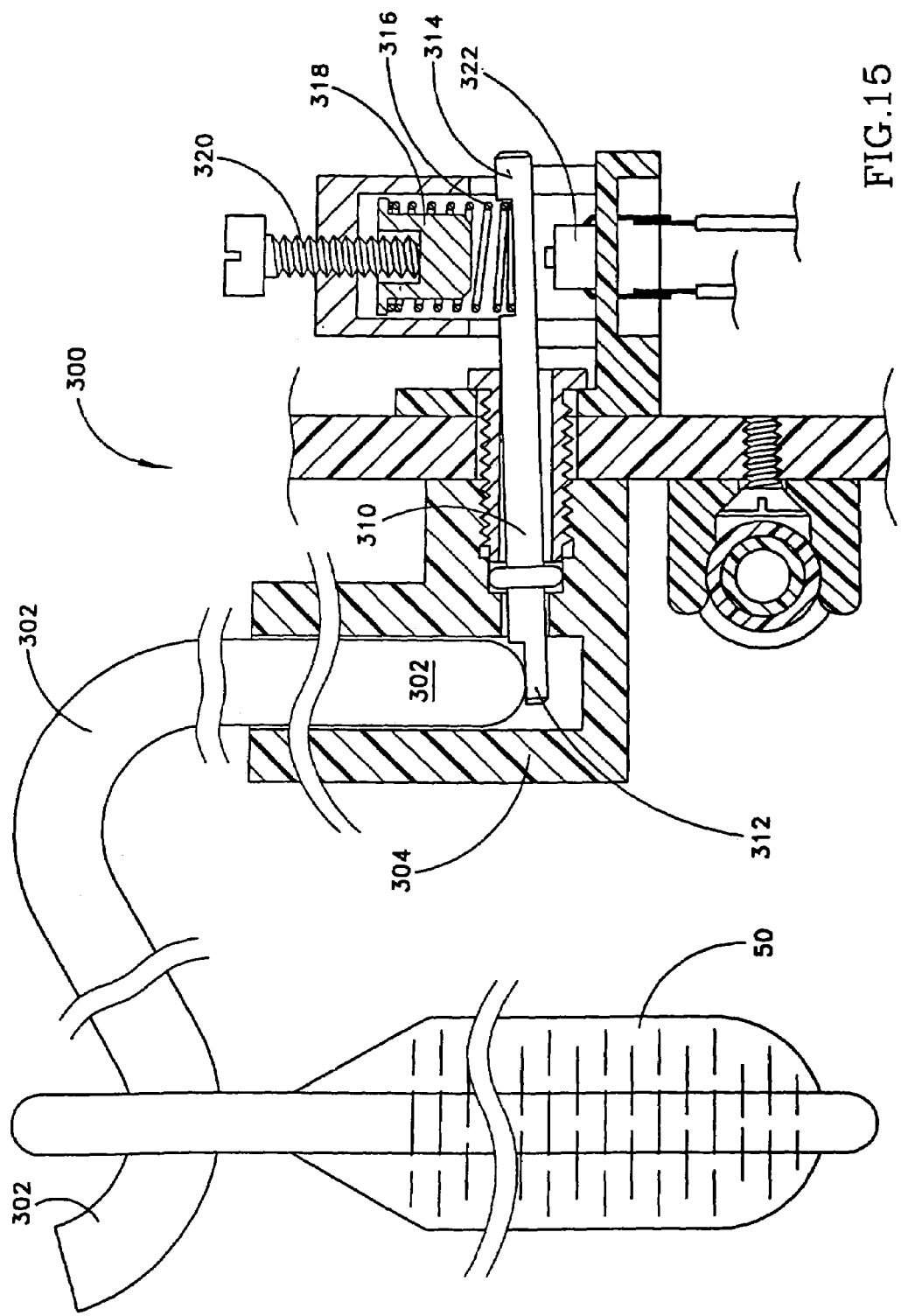
FIGS. 15 and 16 are partial cross-sectional views of embodiments of fluid level detection systems for a system incorporating features of the present invention.
Figure 16:
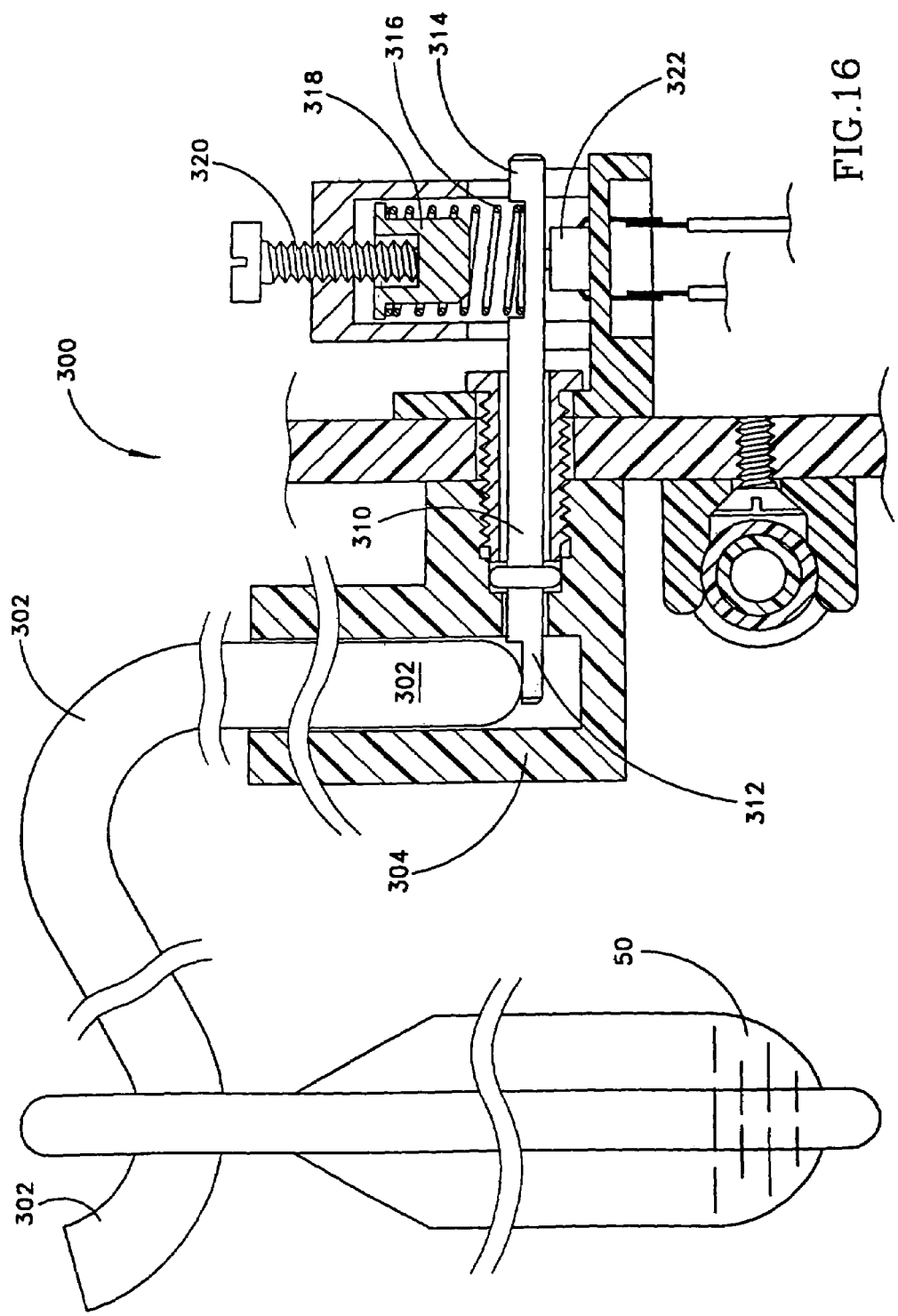

Referring to FIGS. 15 and 16, one embodiment of a fluid level detection system 300 is shown. In FIG. 2, the fluid container 50 is suspended from a mounting pole or member 302. One end of the pole 302 is inserted into a receptacle 304. As shown in FIG. 15, the lower end of the pole member 302 comes to rest against a horizontal beam member 310. The beam member 310 is adapted to pivot around a point (not shown). In one embodiment, one end 312 of the beam member 310 is adapted to move in a downward direction as the combined weight of the fluid bag 50 and the pole member 302 bears down on the end 312 of the beam member 310. The combined weight or force exerted by the fluid bag 50 and the pole member 302 determines the movement or displacement of the end 312. The other end 314 of the beam member 310 is adapted to move in a direction opposite to the movement of the end 312. A bias element 316, such as for example a spring, can be used to apply to the end 314 a biasing force directed in the direction opposite to the direction of movement of the end 314 of the beam member 310. Compressing the bias element 316 using a bolt or screw type device 320 can increase the tension of the bias element 316 and the force that the bias element 316 exerts on the end 314. For example, as shown in FIG. 15, a bolt 320 is inserted into a block 318 and as the bolt 320 is turned, the block 318 moves in a downward direction compressing the spring 316 and increasing its tension. The increased tension of the spring 316 increases the biasing force applied to the end 314. In operation, when a full saline bag is placed on the pole 302, the end 312 is forced by the combined weight of the bag 50 and pole 302 to deflect downward a certain distance. As the fluid in the bag 50 is depleted, the weight of the fluid bag 50 decreases and the end 312 moves in an upward direction while the end 314 moves downward. As shown in FIG. 16, when the fluid level in the saline bag 50 reaches a predetermined level, the end 314 of beam member 310 comes in contact with a switch device 322. The contact of the member 314 with the switch device 322 can cause the fluid alarm unit 630, shown in FIG. 7, to activate visual and audible alarm devices 684 and 682. In an alternate embodiment, any suitable device or mechanism can be used to monitor the fluid level in the saline bag. It is a feature of the present invention to provide a warning to the operator of the system 10 that the fluid level in the fluid supply 50 has reached a predetermined low level.

Figure 17:
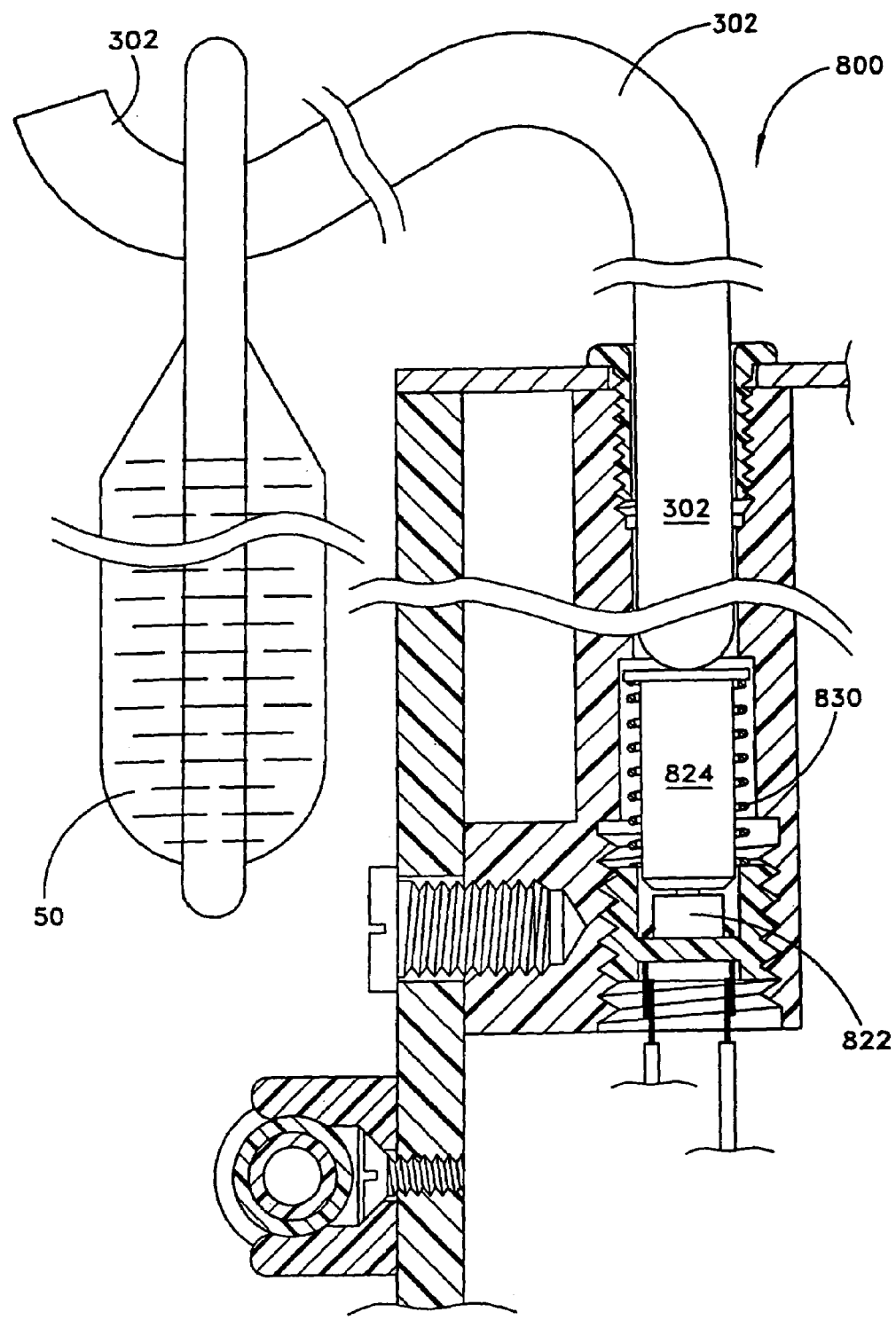
FIGS. 17 and 18 are embodiments of fluid level detection systems for a system incorporating features of the present invention.
Figure 18:
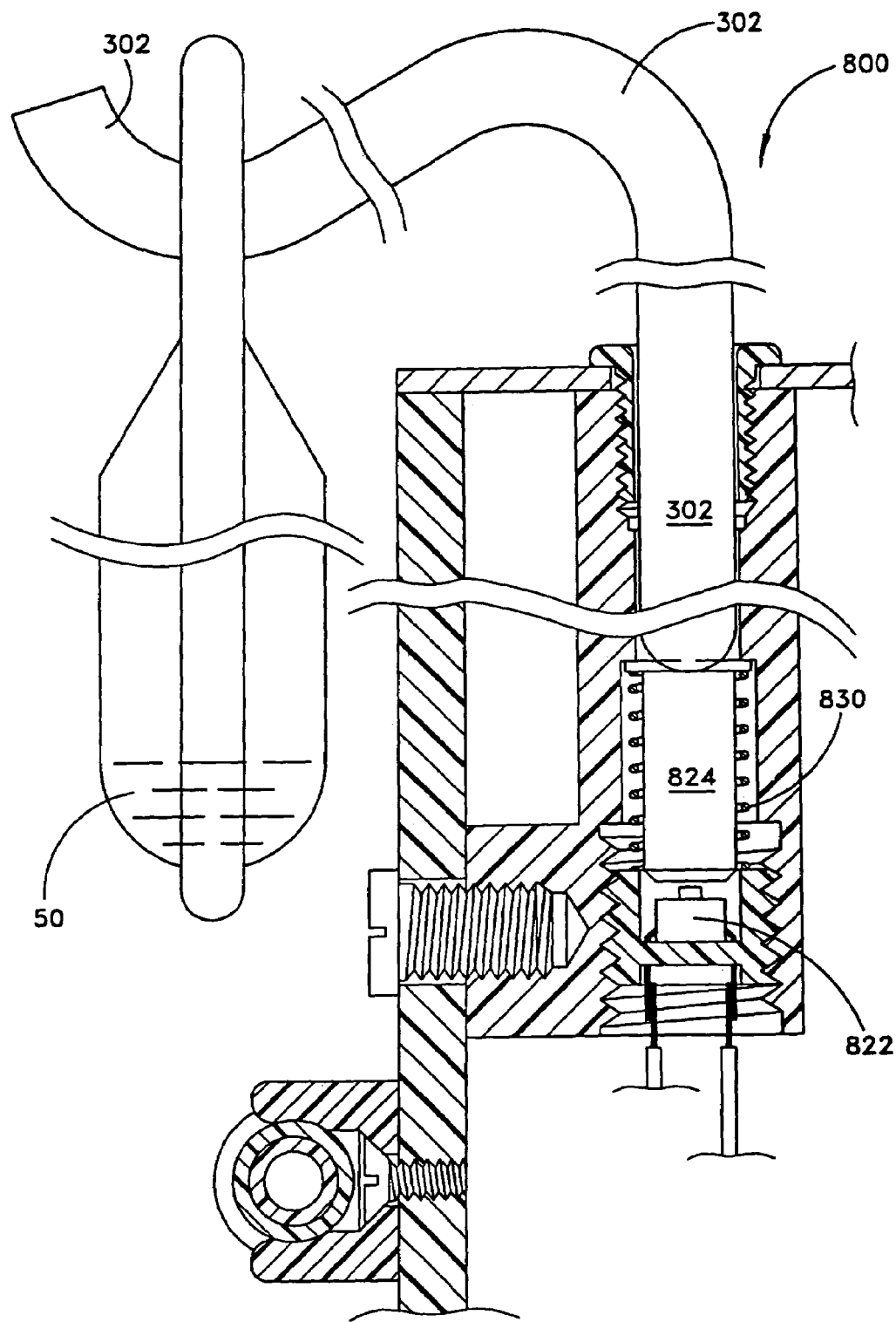

FIGS. 17 and 18 show another embodiment of a fluid level detection system 800. In this embodiment, the pole member 302 rests on a rod 824 that activates switch device 822 when the fluid level in the fluid supply 50 is above a predetermined low level. As the fluid level decreases and reaches a predetermined level, a spring 830 or other biasing element starts to move rod 824 in an upward direction. As shown in FIG. 18, when the fluid level in the fluid bag 50 reaches a predetermined low level, rod 824 gets out of contact with and deactivates switch 822, thereby causing fluid alarm unit 630, shown in FIG. 7, to activate visual alarm device 634 and audible alarm 932.

In the preferred embodiment, audible alarm device 682 is activated with a certain predetermined delay with respect to the visual alarm device 684. Such a sequence of alarms is advantageous in order to limit any disturbance to the patient.

Figure 19:
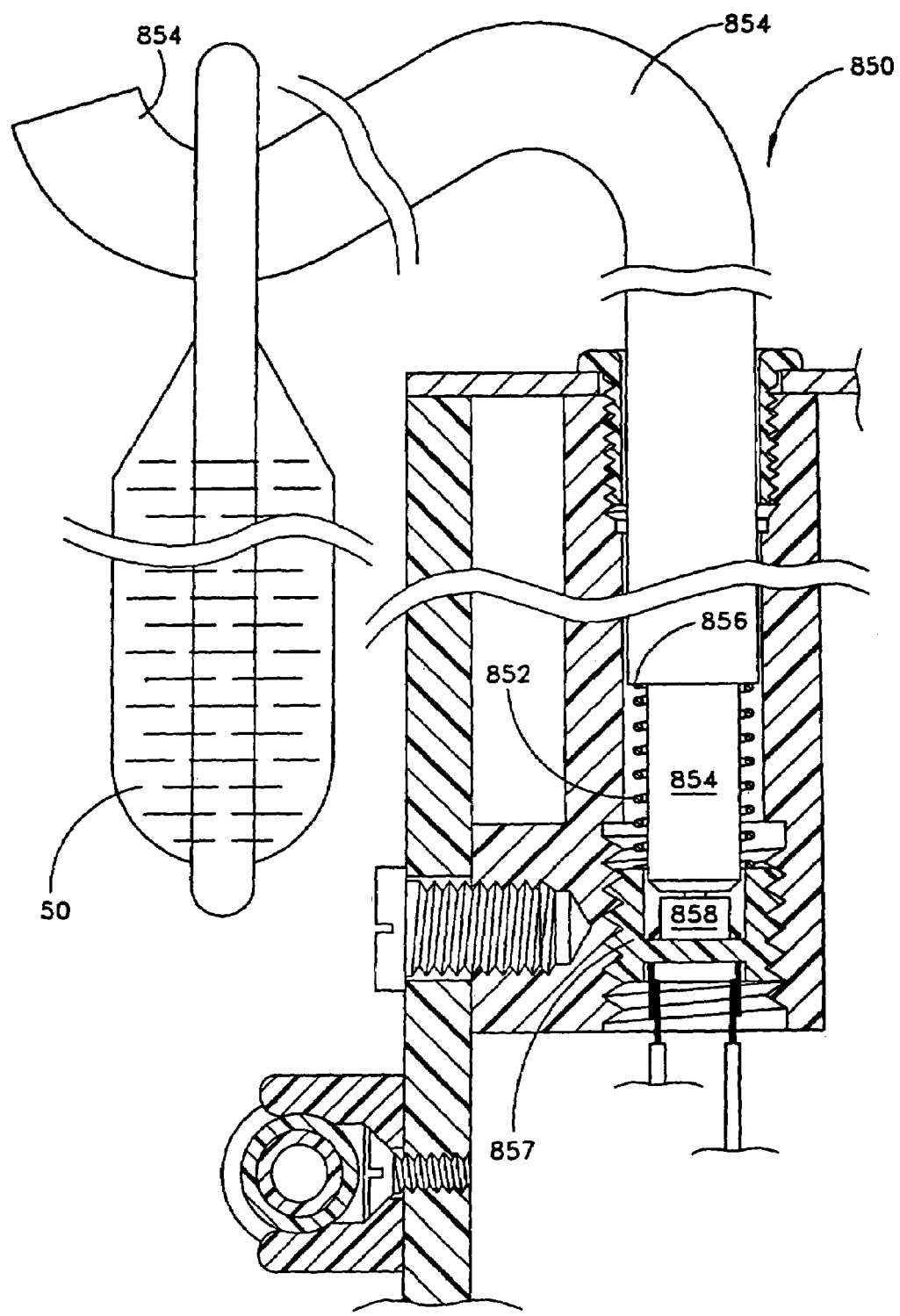
FIGS. 19 and 20 are embodiments of fluid level detection systems for a system incorporating features of the present invention.
Figure 20:
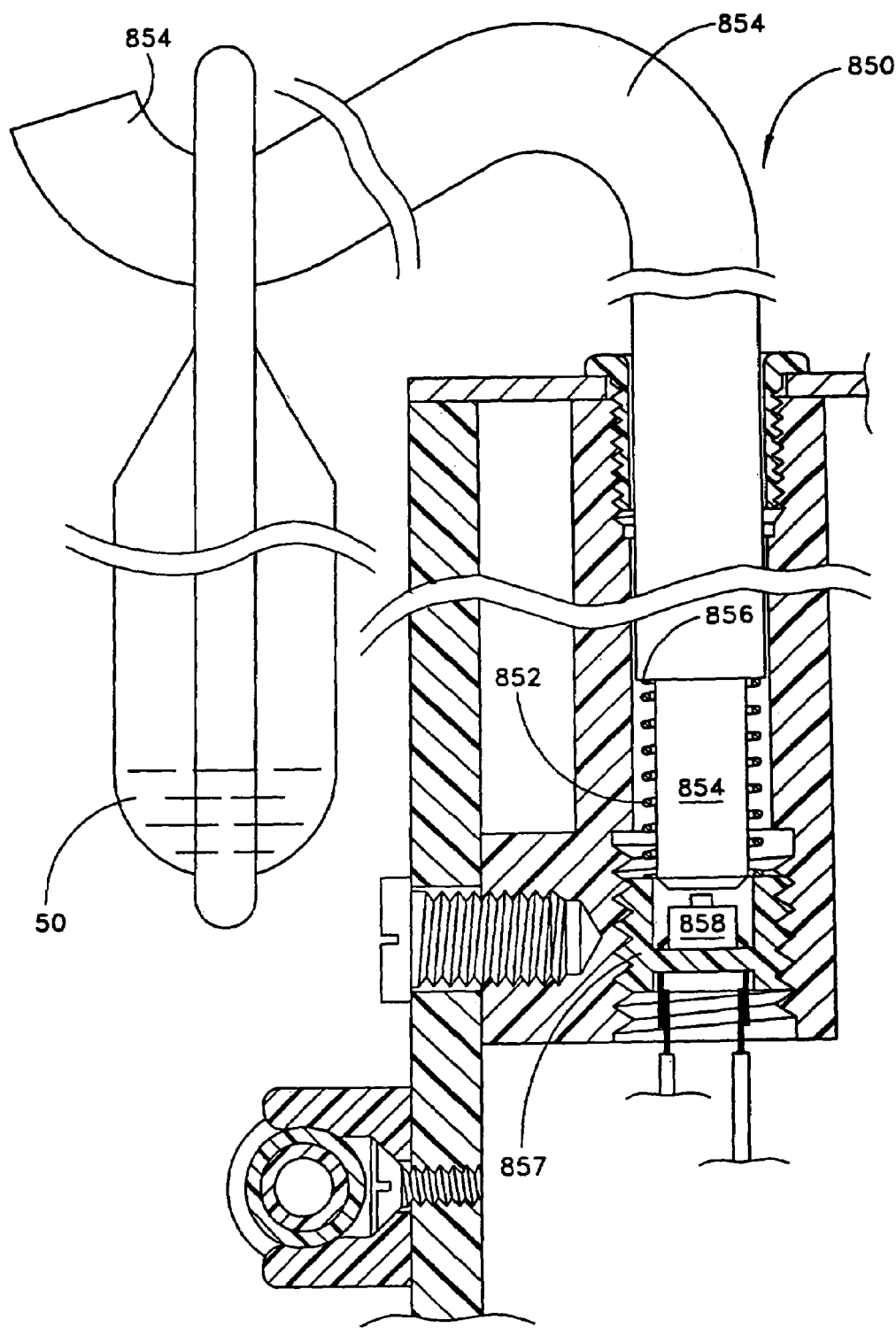

FIGS. 19 and 20 show yet another embodiment of a fluid level detection system 850. In this embodiment a biasing element or spring 852 is disposed around the lower portion of the pole 854. In operation, when a full saline bag 50 is placed on the pole 854, the biasing element 852 becomes compressed between a shoulder 850 of the pole 854 and an adjustment element or screw 857. The combined weight of the full bag 50 and the pole itself will force the lower end of the pole against a switch device 858, thereby providing for direct activation of the switch device 858 by the lower end of the pole.

As shown in FIG. 20, when the fluid level in the bag 50 reaches a predetermined low level, the biasing spring 852 moves the pole 854 in an upward direction, thereby deactivating switch device 858 and causing fluid alarm unit to activate visual and audible alarms.

Figure 21:
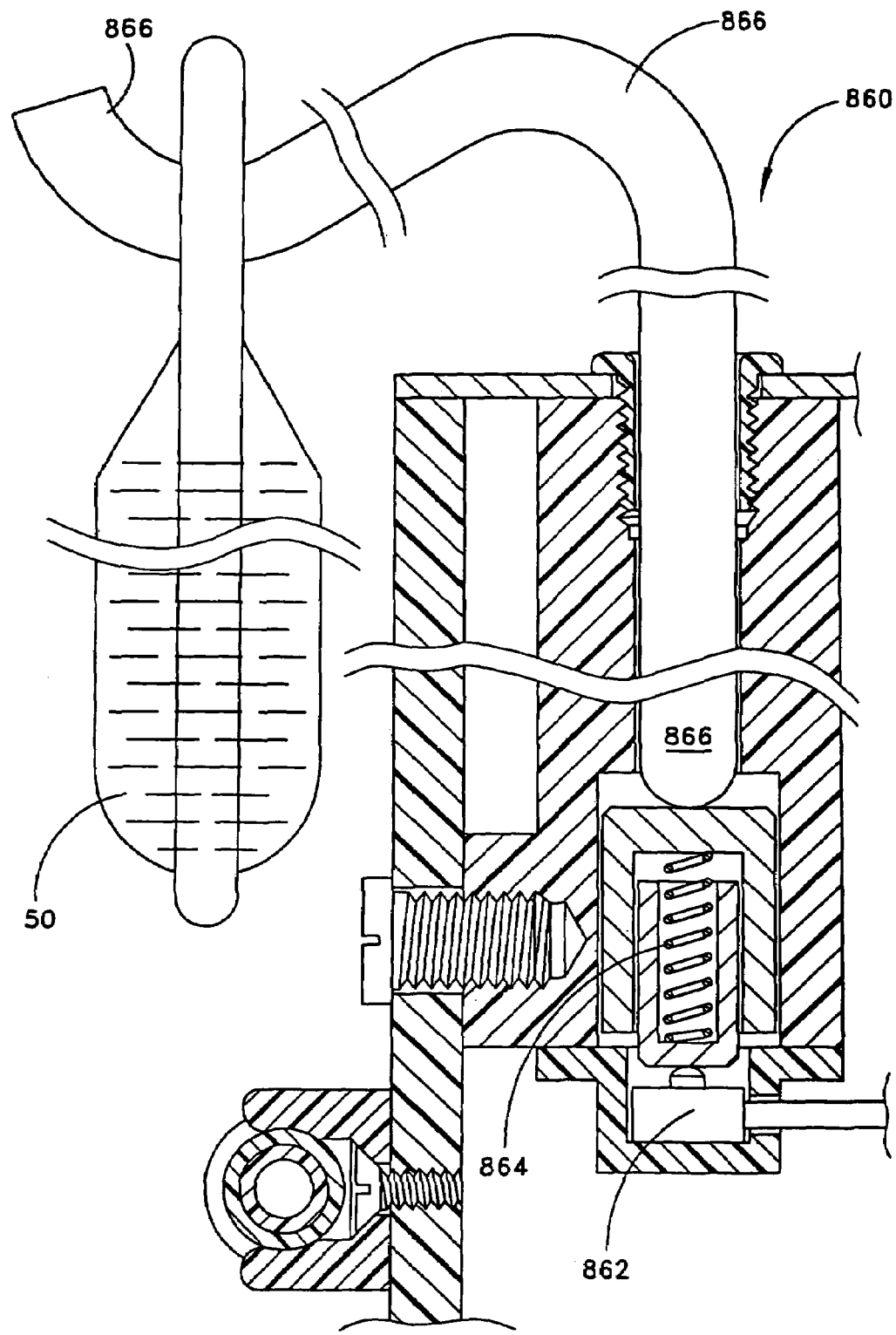
FIGS. 21 and 22 are embodiments of fluid level detection systems for a system incorporating features of the present invention.
Figure 22:
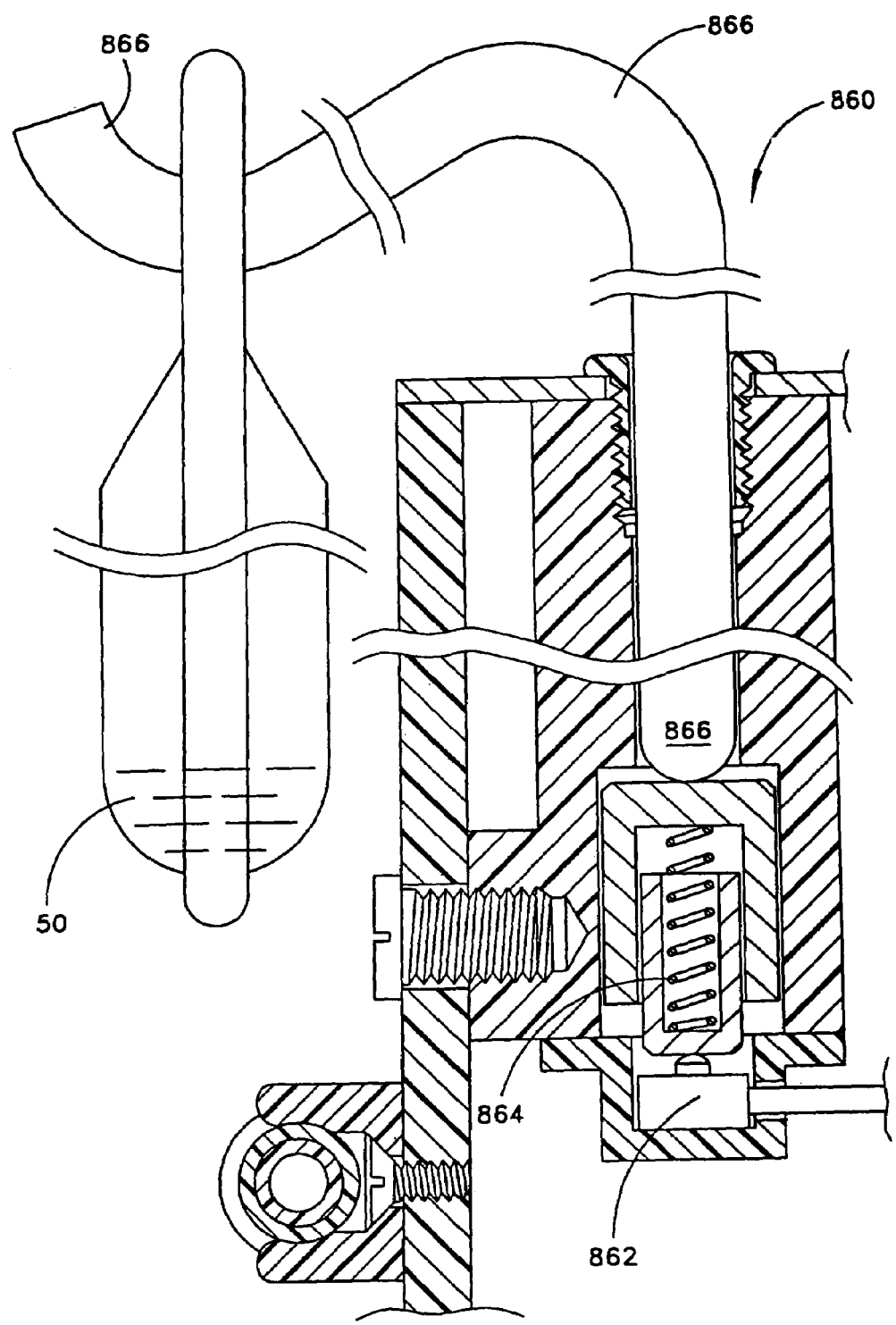
Figure 23:
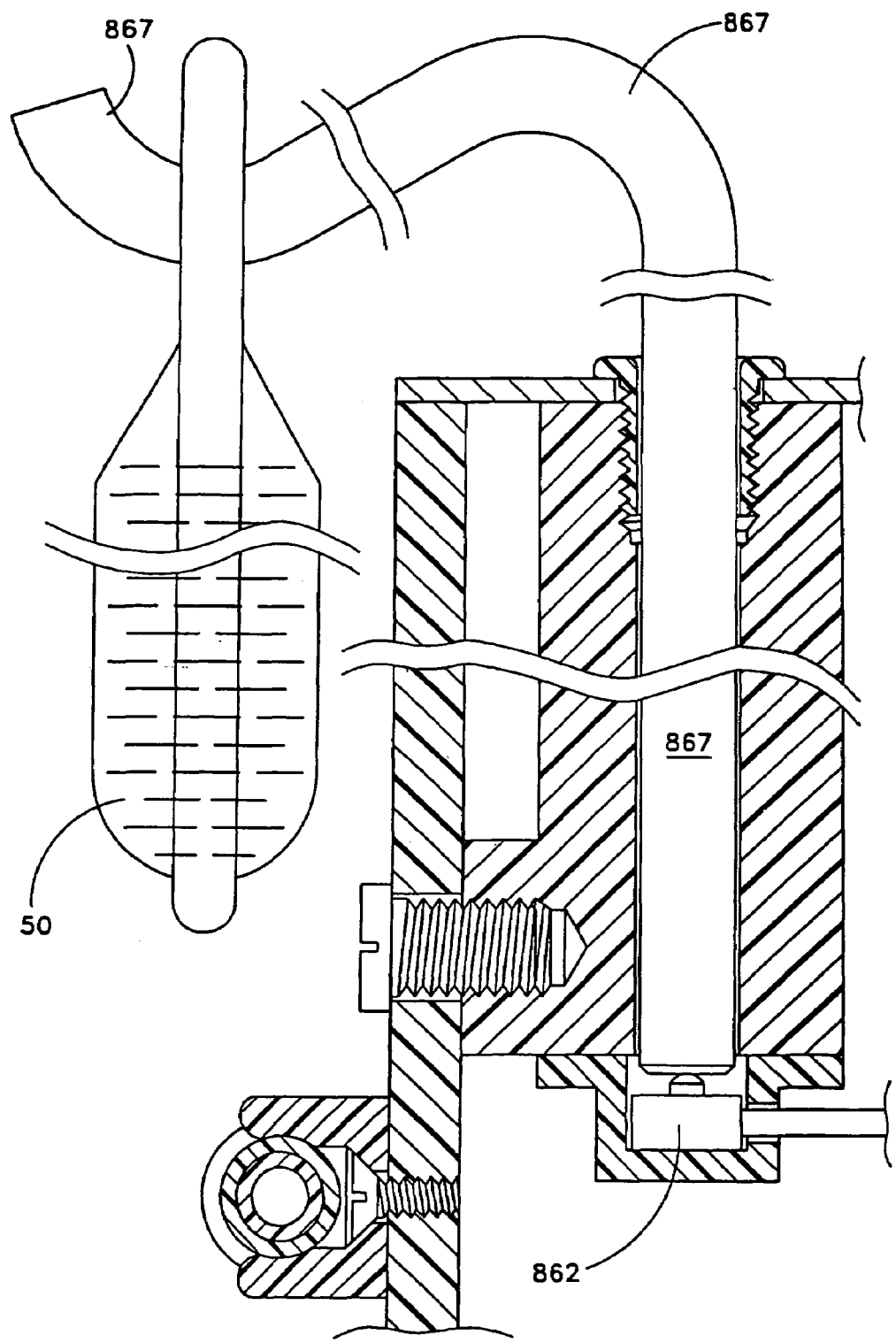
FIG. 23 is one embodiment of a fluid level detection systems for a system incorporating features of the present invention.

FIGS. 21 and 22 show yet another embodiment of a fluid detection system 860 in which a tensiometer device 862 is utilized instead of a switch device. The tensiometer device measures the pressure applied to the device and generates a corresponding electrical signal. A spring type device incorporating e.g. spring 864 can be used to dampen the impact of the pole 866 against the tensiometer device 862 in order to prevent damage to the tensiometer device. However, as shown in FIG. 23, the pole 867 of a modified fluid level detection system 860' can directly contact the tensiometer device 862. In one embodiment, the tensiometer device 862 can include internal mechanisms to dampen the impact on of the pole on the tensiometer device, when, for example, a fluid bag 50 is placed on the pole 867.

As shown in FIG. 7, the controller 60 could also include an input compressed gas pressure sensor(s) combined with a compressed gas shutoff valve(s) 670. In the preferred embodiment, the shutoff valve 670 is generally adapted to shut off the compressed gas supply to the turbine pressure regulator or the controller 60 when the input compressed gas pressure from the system pressure regulator 42 of the compressed gas source 40 exceeds a predetermined level. An additional pressure sensor combined with its own low pressure shutoff valve may be adapted to shut off the compressed gas supply to the turbine pressure regulator 658 or the controller 60 when the input gas pressure is at or below a predetermined level. In addition, input pressure sensors may generate a signal to the pneumatic valve control unit 650 that preclude activation of the turbine pneumatic valve 657 and therefore, the gas turbine 605 of the RAD. The signal from the input pressure sensor(s) may also activate a visual and/or audible alarm device, either directly or indirectly via the pneumatic valve control unit 650. The gas pressure alarm device or gas pressure alarm(s) 673 may be programmed to warn about the input gas pressure being or becoming either too high or too low. Input compressed gas pressure that does not exceed a predetermined upper level, or is within a predetermined range between upper and lower levels is supplied to the turbine pressure regulator 658. A control knob 62 of the turbine pressure regulator 658 is shown in FIG. 2 and can be used to adjust the gas pressure applied to the gas turbine of the RAD.

A turbine pressure sensor and turbine pressure display device 671 can be used to display the gas pressure applied to the gas turbine. The turbine pressure sensor and the turbine pressure display device 671 can be combined into one device, such as for example an analog pressure gauge 61 as shown in FIG. 2. Although the gauge 61 shown in FIG. 2 is illustrated as an analog device, any suitable indicator can be used, such as for example a digital display. In an alternate embodiment, the pressure could be displayed on a system other than the controller 60, such as for example an external display or monitor.

Figure 1:
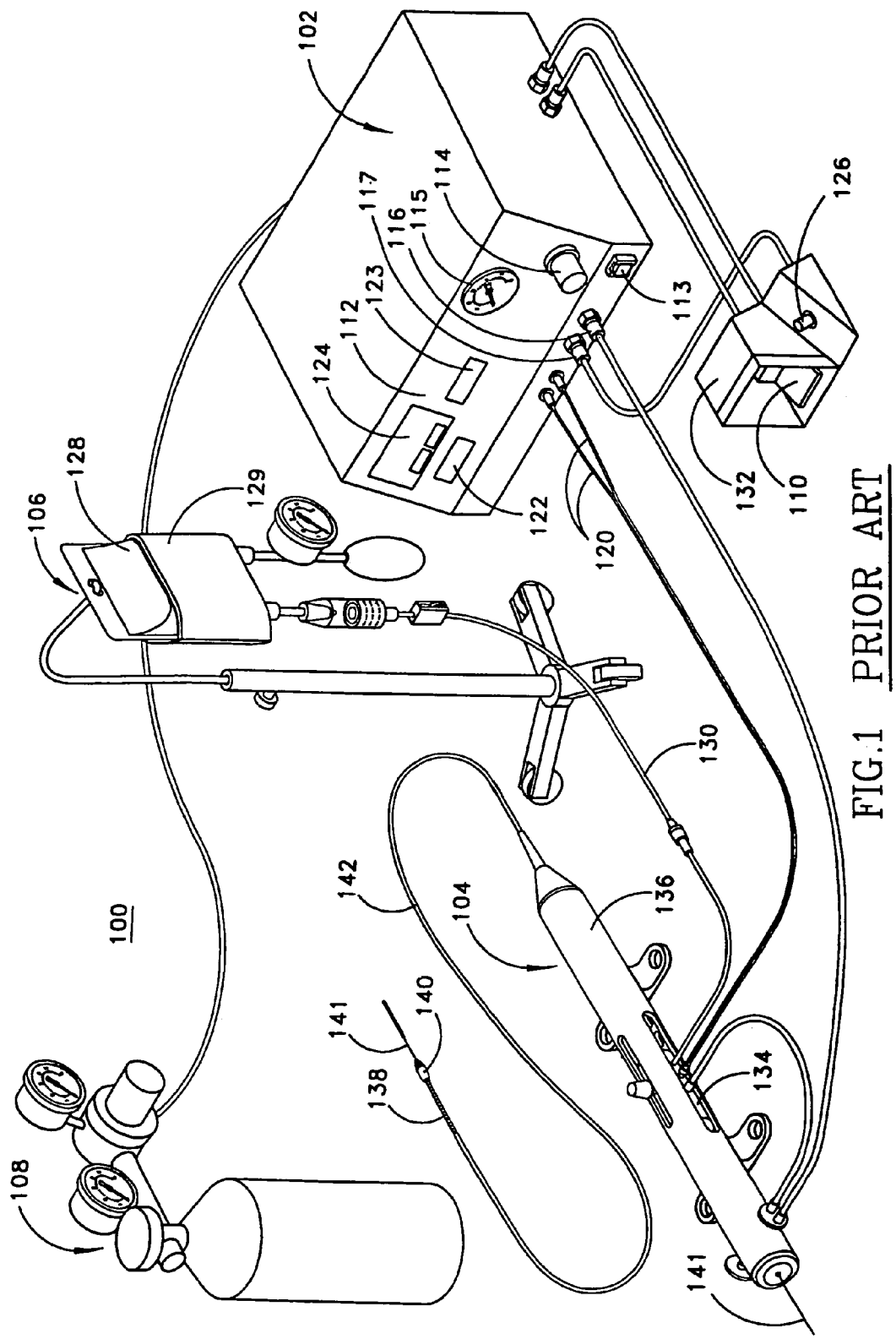
FIG. 1 is a block diagram of a prior art rotational angioplasty device.

The rotational speed of the gas turbine of the RAD shown in FIG. 2 can be monitored by a turbine tachometer 668 shown in FIG. 7. In the preferred embodiment an improved optical tachometer for the RAD, such as that described in U.S. Pat. No. 6,039,747 to Shturman can be used. Referring to FIG. 2, in the preferred embodiment, the optical tachometer 63 utilizes only one optical fiber 23 to conduct both uninterrupted light from the controller 60 to the RAD 20 and pulsed light back to the controller 60. In the rotational angioplasty system of the prior art, shown in FIG. 1 and described in U.S. Pat. No. 5,314,407 to Auth the turbine optical tachometer utilizes two optical fibers. The controller 60 of the present invention can be adapted to interface with this turbine tachometer of the prior art. In an alternative embodiment, any suitable device can be used to monitor the rotational speed of the turbine, including for example optical, electro-optical, electromagnetic and acoustic tachometers can be used.

As shown in FIG. 2, the rotational speed of the turbine of the RAD can be displayed on a turbine tachometer display 63. In the preferred embodiment of the invention, shown in FIG. 2, a digital tachometer display 63 is utilized. In an alternate embodiment, any suitable device, including for example an analog display device, can be used to display the rotational speed of the gas turbine of the RAD.

As shown in FIG. 7, in the preferred embodiment, the controller 60 may also include a tachometer test device 674 to test for adequate function of that portion of the turbine tachometer that is located in the controller 60. A pushbutton switch could be included on the controller 60 for this purpose.

In one embodiment, as shown in FIG. 7, the turbine tachometer 668 can be coupled or connected to the pump control unit 610. The turbine tachometer 668 could provide an input signal to the pump control unit 610, thereby causing adjustment of the rotational speed of the fluid pump motor 612 depending on the rotational speed of the gas turbine.

Figure 24:
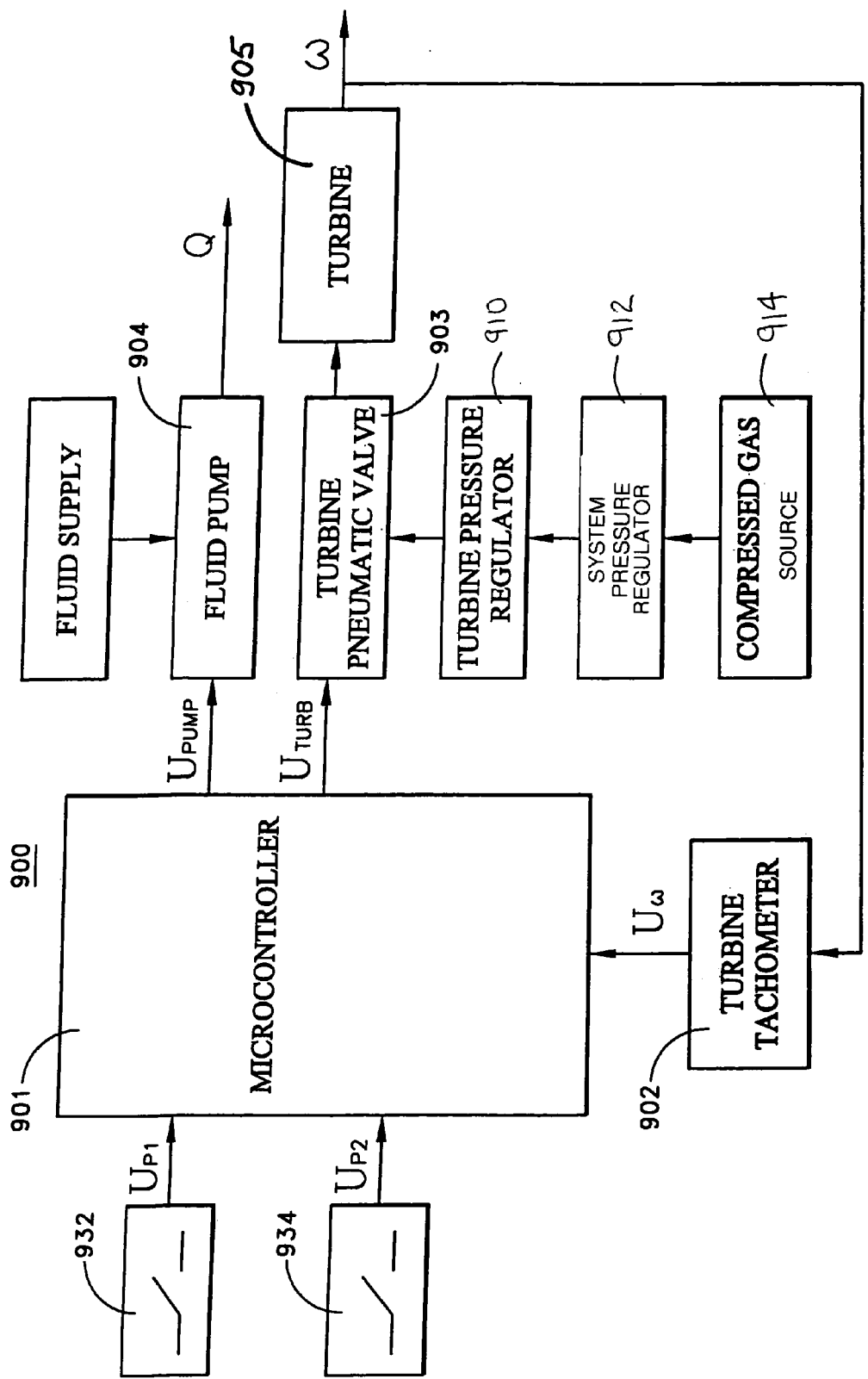
FIG. 24 is a block diagram of one embodiment of a control system for a system incorporating features of the present invention.

It should be understood that although the switches 32 and 34 in FIG. 2, and similar switches in FIGS. 7 and 24, are shown as two separate pedal activated switches, any suitable switching device(s) can be used, including a switching device comprising a single switch.

Referring to FIG. 24, one embodiment of a control system 900 for controlling fluid pump 904 and gas turbine 305 of rotational angioplasty device is illustrated. As shown in FIG. 24, a microcontroller 901, receives a combination of inputs comprising $U_{P1}$ from pump pedal switch 932 (which is similar to the fluid pump pedal switch 32 in FIG. 2), $U_{P2}$ from turbine pedal switch 934 (which is similar to the turbine pedal switch 34 in FIG. 2), and a turbine speed signal $U\omega$ from a turbine tachometer 902. It should be understood that the microcontroller based control system shown in FIG. 24 can be programmed to perform substantially all of the functions of the control system shown in FIGS. 2 and 7. In particular, in one embodiment, the microcontroller 901 can be programmed to activate a turbine pneumatic valve 903 only if the fluid pump 904 was activated to pump saline at an accelerated rate for at least a minimum predetermined period of time using the pump pedal switch 932 and if the turbine pedal switch 934 was activated within a predetermined time period $t_{delay}$ after the pump pedal switch 932 has been deactivated.

As shown in FIG. 25, a single pedal activated switch 1010 could be used to control microcontroller 1001 where a first switch activation establishes a first mode of operation for the system 1000 (e.g. the fluid pump 1004 is "ON"). A second switch activation establishes a second mode of operation for the system 1000 (e.g. both the fluid pump 1004 and the gas turbine 1005 are "ON" or active). A third switch activation returns the system to its "static" state where the fluid pump is at minimum or "min" flow rate and the gas turbine is "OFF."

An example of a single pedal switch 1101 is shown in FIG. 26. All other elements of the system 1100 shown in FIG. 26 are similar and have the same numbers as the elements of the system 10 shown in FIG. 2.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A controller for a rotational atherectomy system comprising:
    a fluid pump control device adapted to control a pumping of a fluid through a rotational atherectomy device;
    wherein the fluid pump control device comprises:
        a fluid flow controller adapted to provide a pump control signal to a fluid pump;
        a first control device adapted to provide a pump activation signal to the fluid flow controller; and
        a second control device adapted to provide a turbine activation signal to the fluid flow controller and the turbine control device;
        wherein upon activation of the first control device the fluid pump is activated to pump the fluid at a dynamic fluid flow rate and
        upon activation of the second control device within a predetermined time interval the fluid pump continues pumping the fluid at the dynamic fluid flow rate while the drive shaft rotation is initiated and maintained;
    a turbine control device adapted to control a rotation of a drive shaft of the rotational atherectomy device; and
    an alarm device adapted to provide an alarm indication if a fluid supply level to the system is below a predetermined level, wherein the alarm device is adapted to prevent the rotation of the drive shaft if the alarm device is activated prior to activation of the second control device.

2. The controller of claim 1 wherein the pumping of fluid to the rotational atherectomy device is substantially independent upon the rotational speed of the drive shaft.

3. The controller of claim 1 wherein the rotation of the drive shaft is dependent upon the pumping of fluid through the atherectomy device.

4. The controller of claim 1 wherein the rotation of the drive shaft is dependent upon the pumping of fluid to the driveshaft of atherectomy device.

5. The controller of claim 1 wherein the fluid flow controller further includes a fluid flow delay device adapted to delay the pump from changing from the dynamic flow rate to a static fluid flow rate for a predetermined time period after a deactivation of the first control device.

6. The controller of claim 1 wherein the fluid flow controller is further adapted to provide a turbine block signal to the turbine control device, adapted to prevent the rotation of the drive shaft if the second control device is not activated prior to an expiration of a predetermined time period after a deactivation of the first control device.

7. The controller of claim 1 wherein the fluid flow controller is further adapted to enable an activation signal for the rotation of the drive shaft when the second control device is activated before an end of a predetermined time period after the deactivation of the first control device.

8. The controller of claim 1 wherein the first control device comprises a foot activated switch having an on position and an off position.

9. The controller of claim 1 wherein the second control device comprises a foot activated switch having an on position and an off position.

10. The controller of claim 1 wherein the fluid flow controller is further adapted to delay a change in the state of the fluid pump for a second predetermined time period following a deactivation of the second control device.

11. The controller of claim 1 wherein the fluid flow controller is adapted to maintain the state of the pump at a static flow rate during a period of time when the drive shaft is not rotating.

12. The controller of claim 1 further comprising a fluid level monitoring device adapted to detect a level of a fluid supply for the rotational atherectomy system and activate an alarm device if the fluid falls below a predetermined level.

13. The controller of claim 1 further comprising a pump status device adapted to detect an open position of a pump in the rotational atherectomy system and activate an alarm device if the pump is in the open position.

14. The controller of claim 1 further comprising the alarm device including an alarm indicator.

15. The controller of claim 14 wherein the alarm indicator is an audible alarm.

16. The controller of claim 1 wherein the alarm device is adapted to stop the rotation of the drive shaft if the alarm device is activated.

17. The controller of claim 1 wherein the control signal is adapted to cause the pump to pump at a dynamic flow rate or a static flow rate.

* * * * *